United States Patent
Wong et al.

(10) Patent No.: US 9,763,889 B2
(45) Date of Patent: Sep. 19, 2017

(54) ORAL DELIVERY SYSTEM FOR HEMOGLOBIN BASED OXYGEN CARRIERS

(71) Applicant: Billion King International Ltd., Hong Kong (HK)

(72) Inventors: Bing Lou Wong, Irvine, CA (US); Sui Yi Kwok, Hong Kong (HK)

(73) Assignee: Billion King International Ltd., Hong Kong (HK)

( * ) Notice: Subject to any disclaimer, the term of this patent is extended or adjusted under 35 U.S.C. 154(b) by 0 days.

(21) Appl. No.: 15/016,220

(22) Filed: Feb. 4, 2016

(65) Prior Publication Data

US 2016/0375141 A1    Dec. 29, 2016

Related U.S. Application Data

(63) Continuation-in-part of application No. 14/754,668, filed on Jun. 29, 2015.

(51) Int. Cl.

| A61K 47/36 | (2006.01) |
|---|---|
| A61K 38/42 | (2006.01) |
| A61K 9/28 | (2006.01) |
| A61K 9/19 | (2006.01) |
| A61K 9/48 | (2006.01) |
| A61K 9/51 | (2006.01) |
| A61K 45/06 | (2006.01) |
| A61K 9/20 | (2006.01) |
| A61K 9/00 | (2006.01) |
| B82Y 5/00 | (2011.01) |

(52) U.S. Cl.
CPC .......... *A61K 9/4891* (2013.01); *A61K 9/0095* (2013.01); *A61K 9/19* (2013.01); *A61K 9/2095* (2013.01); *A61K 9/2846* (2013.01); *A61K 9/2866* (2013.01); *A61K 9/4833* (2013.01); *A61K 9/5161* (2013.01); *A61K 38/42* (2013.01); *A61K 45/06* (2013.01); *B82Y 5/00* (2013.01)

(58) Field of Classification Search
None
See application file for complete search history.

(56) References Cited

U.S. PATENT DOCUMENTS

| 5,929,031 | A * | 7/1999 | Kerwin | C07K 14/805 |
|---|---|---|---|---|
| | | | | 514/13.4 |
| 6,399,116 | B1 | 6/2002 | Xiu | |
| 7,932,356 | B1 | 4/2011 | Wong et al. | |
| 7,989,593 | B1 | 8/2011 | Wong et al. | |
| 8,048,856 | B1 | 11/2011 | Wong et al. | |
| 8,084,581 | B1 | 12/2011 | Wong et al. | |
| 8,106,011 | B1 | 1/2012 | Wong et al. | |
| 2010/0144595 | A1 * | 6/2010 | Bucci | A61K 38/42 |
| | | | | 514/3.8 |

OTHER PUBLICATIONS

Silva et al (AAPS Journal (Jan. 13, 2006), 7(4) Article 88, pp. E903-E913).*
Shaji J et al (Indian J Pharm Sci (2008) 70(3):269-77.*
Fenyvesi (Cyclodexrin News (Sep. 2011) 25:9).*
Stratton (Hemoglobin: international journal for hemoglobin research (1988) 12(4)).*
Morengo-Rowe (Proc Bayl Univ Med Cent (2006) 19(3):239-245).*
Gupta (Journal of Controlled Release (Dec. 10, 2013) 172(2): 541-549).*
WebMD "Mountain Sickness Treatment", available at http://www.webmd.com/first-aid/mountain-sickness-treatment#2, accessed on Jan. 17, 2017.*
Artursson, P., et al. "Effect of chitosan on the permeability of monolayers of intestinal epithelial cells (Caco-2)." Pharm Res., 1994, 11: 1358-1361.
Ballard, T.S., et al. "Regulation of tight-junction permeability during nutrient absorption across the intestinal epithelium." Annu. Rev. Nutr, 1995, 15: 35-55.
Bamikol, W.K., et al. "Complete healing of chronic wounds of a lower leg with haemoglobin spray and regeneration of an accompanying severe dermatoliposclerosis with intermittent normobaric oxygen inhalation (INBOI): a case report." Ger Med Sci., 2011, 9 (DOI: 10.3205/000131).
Barrett, K.E., et al. "New Delhi: Tata-McGraw-Hill." Ganong's Review of Medical Physiology, 2009, 23rd edition, pp. 619-620.
Bonaventura, C., et al. "Allosteric effects on oxidative and nitrosative reactions of cell-free hemoglobin." IUBMB Life, 2007, 59(8-9): 498-505.
Brunel, F., et al. "Self-assemblies on chitosan nanohydrogels." Macromol Biosci., 2010, 10(4): 424-432.
Cicco, G., et al. "Wound healing in diabetes: hemorheological and microcirculatory aspects." Adv Exp Med Biol. 2011, 701: 263-269.
Dünnhaupt, et al. "Distribution of thiolated mucoadhesive nanoparticles on intestinal mucosa." International Journal of Pharmaceutics, 2011, 408 (1-2): 191-199.

(Continued)

*Primary Examiner* — Marcela M Cordero Garcia
*Assistant Examiner* — Catherine Mader
(74) *Attorney, Agent, or Firm* — Spruson & Ferguson HK

(57) ABSTRACT

A process for making hemoglobin based oxygen carrier (HBOC) containing pharmaceutical composition suitable for oral delivery and the composition formed thereby are described. There are three exemplary composition configurations which include (1) hemoglobin-loaded nanoparticles solution, (2) enteric-coated hemoglobin capsules and (3) enteric-coated hemoglobin tablets. To facilitate the bioavailability and bio-compatibility of hemoglobin, intestinal absorption enhancers are added in each of the HBOC formulations. Protective layers ensure delivery of an intact hemoglobin structure in intestinal tract without degradation in the stomach. The HBOC formulations may be used for preventive or immediate treatment of high altitude syndrome (HAS) or for treatment of hypoxic conditions including blood loss, anemia, hypoxic cancerous tissue, and other oxygen-deprivation disorders. In addition to delivering oxygen, the heme group of hemoglobin from HBOC formulations can provide heme iron to the human body to aid in the production of more red blood cells. The presently claimed invention provides improved hemoglobin formulations for forming nanoparticles with improved properties via polyelectrolyte complexation and for lyophilization to form mixture powder or particles with improved properties.

15 Claims, 16 Drawing Sheets

(56) References Cited

OTHER PUBLICATIONS

Hackett, P.H., et al. "Dexamethasone for prevention and treatment of acute mountain sickness." Aviat space Environ Med., 1988, 59: 950-954.
Hiromi, Sakai, et al. "Review of Hemoglobin-Vesicles as Artificial Oxygen Carriers." Artificial organs, 2009, 33(2): 139-145.
Iwasaki, N, et al. "Feasibility of polysaccharide hybrid materials for scaffolds in cartilage tissue engineering: evaluation of chondrocyte adhesion to polyion complex fibers prepared from alginate and chitosan." Biomacromolecules, 2004, 5(3): 828-833.
Levien, L.J. "South Africa: clinical experience with Hemopure." ISBT Science Series, 2006, 1(1): 167-173.
Lin, Y.H., et al. "Multi-ion-crosslinked nanoparticles with pH-responsive characteristics for oral delivery of protein drugs." J Control Release., 2008: 132(2), 141-149.
Makhlof, A., et al. "Design and evaluation of novel pH-sensitive chitosan nanoparticles for oral insulin delivery." Eur J Pharm Sci., 2011, 42(5): 445-451.
Natanson, C., et al. "Cell-free hemoglobin-based blood substitutes and risk of myocardial infarction and death—A meta-analysis." J Amer. Med. Assoc., 2008, 299(19): 2304-2312.
Niederhofer, A., et al. "A method for direct preparation of chitosan with low molecular weight from fungi." Eur J Pharm Eliopharm, 2004, 57: 101-105.
Paralikar, Swapnil J., et al. "High-altitude medicine." Indian J Occup Environ Med., 2010, 14(1): 6-12.
Remy, B., et al., "Red blood cell substitutes: fluorocarbon emulsions and hemoglobin emulsions." British Medical Bulletin, 1999, 55: 277-298.
Richard, A., et al. "Poly(glutamic acid) for biomedical applications." Crit Rev Biotechnol, 2001, 21: 219-232.
Sonaje, K., et al. Enteric-coated capsules filled with freeze-dried chitosan/poly(gamma-glutamic acid) nanoparticles for oral insulin delivery. Biomaterials, 2010, 31(12): 3384-3394.
Sudarshan, N., et al. "Antibacteri action of chitosn." Food Biotechnology, 1992, 6(3): 257-272.
Baek et al. "Hemoglobin-driven pathophysiology is an in vivo consequence of the red blood cell storage lesion that can be attenuated in guinea pigs by haptoglobin therapy." The Journal of Clinical Investigation, 2012, 122(4): 1444-1458.
Becket, G., et al. "Improvement of the in vitro dissolution of praziquantel by complexation with $\alpha$-, $\beta$-, $\gamma$-cyclodextrins." International Journal of Pharmaceutics, 1999, 179(1): 65-71.
Blancher, C., et al. "Relationship of Hypoxia-inducible Factor (HIF)-1$\alpha$ and HIF-2$\alpha$ Expression to Vascular Endothelial Growth Factor Induction and Hypoxia Survival in Human Breast Cancer Cell Lines." Cancer Res., 2000, 60: 7106-113.
Gupta, V., et al. "A permeation enhancer for increasing transport of therapeutic macromolecules across the intestine." Journal of Controlled Release, 2013, 172(2): 541-549.
Honary, S., et al. "Effect of zeta potential on the properties of nano-drug delivery systems—a review (part 2)". Tropical Journal of Pharmaceutical Research, 2013, 12 (2): 263-273.
Yamamoto, A., et al. "Effects of various protease inhibitors on the intestinal absorption and degradation of insulin in rats." Pharmaceutical Research, 1994, 11(10): 1496-1500.

\* cited by examiner

ORAL DELIVERY SYSTEM FOR HEMOGLOBIN BASED OXYGEN CARRIERS

COPYRIGHT NOTICE/PERMISSION

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever. The following notice applies to the processes, experiments, and data as described below and in the drawings attached hereto: Copyright© 2012-15, Billion King International Limited, All Rights Reserved.

TECHNICAL FIELD

The present invention relates to a process for making hemoglobin based oxygen carrier (HBOC) containing pharmaceutical compositions suitable for oral delivery and the compositions produced thereby. The orally-deliverable HBOC compositions are suitable for treating a variety of conditions where enhanced tissue oxygenation is desirable.

BACKGROUND OF INVENTION

Hemoglobin plays an important role in most vertebrates for gaseous exchange between the vascular system and tissue. It is responsible for carrying oxygen from the respiratory system to the body cells via blood circulation and also carrying the metabolic waste product carbon dioxide away from body cells to the respiratory system, where the carbon dioxide is exhaled. Since hemoglobin has this oxygen transport feature, it can be used as a potent oxygen supplier if it can be stabilized ex vivo and used in vivo.

Development of hemoglobin based oxygen carriers (HBOCs) has been pursued as an alternative to treatment with whole blood products. Typically, past HBOCs have been used as resuscitative fluids for hemorrhagic shock in emergency situations. However, there are various complications that have prevented widespread use of HBOCs. Such complications include extravasation of small-sized hemoglobin, myocardial infarction, hypertension, and renal toxicity (Bonaventura et al., 2007; Natanson et al., 2008). Various attempts to stabilize and purify the hemoglobin in HBOCs have yielded promising results; however, there is still no FDA-approved HBOC for routine clinical use.

While substantial research has been devoted to HBOC formulations for intravenous delivery, such intravenous delivery can be inconvenient or impossible in non-hospital settings. Therefore, there is a need in the art for HBOC compositions that can be delivered orally in non-hospital settings. Such compositions can be used to treat conditions where enhanced tissue oxygenation is desirable either due to medical or environmental conditions.

One environment where enhanced oxygenation is desirable is at high altitudes. High altitude syndrome (HAS) typically appears on rapid ascent to an altitude above 2,500 meters. Every day thousands of people travel to high altitudes, such as mountainous regions, and about 20% of them experience symptoms of HAS including headache, nausea, dizziness and sleep difficulty. Normally, the symptoms are sufficiently mild that they can be relieved by limiting activity and remaining at the same altitude for a few days for acclimatization. Without proper acclimatization and continuing to ascend, the sickness may progress to high altitude cerebral edema or high altitude pulmonary edema which is life threatening conditions that need to be treated aggressively (Paralikar, 2010).

Lower oxygen levels at high altitude increases ventilation by stimulating peripheral chemoreceptors, leading to hyperventilation. Hyperventilation reduces the alveolar carbon dioxide level, resulting in hypocapnia and alkalosis of blood. At the same time, cerebral blood flow increases to ensure adequate oxygen delivery. The resultant change in blood pH and the increase of cerebral pressure cause the mild symptoms described above. In response to the hypoxic environment, the human body initiates a series of adaptive mechanisms, i.e. acclimatization. For instance, the kidney excretes excessive bicarbonate and conserves hydrogen ions. Finally, blood and cerebrospinal fluid pH as well as ventilation rate are restored. Another important regulation is that hypoxia stimulates the release of the hormone erythropoietin from the kidney. Erythropoietin-sensitive committed stem cells in the bone marrow are stimulated to differentiate into red blood cells (RBC). New RBC can be generated and circulated in the blood stream within 4-5 days (Barrett et al., 2009). Long-term acclimatization leads to an increase in blood volume and RBC cell mass, therefore the oxygen-carrying capacity can be increased. Blood alkalosis shifts the oxygen-hemoglobin dissociation curve to the left. Meanwhile, a concomitant increase in RBC 2,3-diphosphoglycerate shifts the curve to the right. As a result, a net increase in p50 (affinity between hemoglobin and oxygen decreases) increases $O_2$ available to tissues (Barrett et al., 2009).

There have been various approaches taken in the past to treat HAS. Treatment with acetazolamide increases the rate of acclimatization (Paralikar, 2010). Acetazolamide, a renal carbonic anhydrase inhibitor, reduces bicarbonate re-absorption to maintain the balance of hydrogen ions. Moreover, acetazolamide inhibits cerebrospinal fluid production and reduces cerebrospinal fluid pressure. Steroids, particularly dexamethasone, have also been found to be effective in relieving symptoms (Hackett et al., 1988). However, both drugs (acetazolamide and steroids) are not targeting at enhancing cellular oxygen delivery to alleviate the condition. Additionally there have been reports that the Chinese herbal medicine *Rhodiola* can enhance blood oxygen levels (Xiu, 2002). However, there are side effects to *Rhodiola* including irritability, restlessness, and insomnia.

Regarding HBOCs, there have been some attempts to create alternative delivery mechanisms for the hemoglobin. One approach formulates hemoglobin-vesicles that mimic the cellular structure of RBC. Hemoglobin-vesicles are formed by encapsulating hemoglobin within a thin lipid bilayer membrane. However, such formulations, as with prior art HBOCs, are designed for intravenous delivery.

Oral drug delivery is convenient for patients, particularly in non-clinical settings; however several potential problems need to be solved, especially for protein-based drugs such as HBOCs. First, peptides or proteins can be degraded and digested by low pH gastric medium in the stomach and proteases in pancreatic juice. Second, the absorption of peptides or proteins in the intestine is hindered by their high molecular weight and hydrophilicity. Thus there is a need in the art for oral delivery HBOC compositions to ensure safe and effective delivery of oxygen to patients having a need for enhanced oxygen transport. Such a composition could be used to treat patients having HAS or other hypoxic conditions including blood loss, anemia, hypoxic cancerous tissue, and other oxygen-deprivation-based disorders.

SUMMARY OF INVENTION

The present invention relates to processes for making hemoglobin based oxygen carrier (HBOC) containing pharmaceutical compositions suitable for oral delivery and to the hemoglobin based oxygen carriers produced thereby. The formulations of the invention have particular application for preventive or immediate treatment of high altitude syndrome (HAS) by oxygen delivery; however, the oral formulations of the present invention can be used in any situation where it is desirable to enhance oxygen delivery to tissue with a HBOC such as for treatment of hypoxic conditions including blood loss, anemia, hypoxic cancerous tissue, and other oxygen-deprivation disorders.

The present HBOC formulations use hemoglobin-loaded nanoparticles capsules or tablets to facilitate the bioavailability and bio-compatibility of the hemoglobin. Protective layers in different configurations assure intact structure of hemoglobin, without degradation in stomach. Optional additional excipients can be added for time-release or controlled-release compositions or for composition preservation and/or stabilization.

In one embodiment a hemoglobin-based oxygen carrier is orally delivered to a subject in need thereof by providing at least one of the following delivery systems containing the hemoglobin based oxygen carrier: a nanoparticle solution, an enteric-coated capsule, and/or an enteric-coated tablet. The delivery system is configured such that the hemoglobin based oxygen carrier is released in the intestinal tract and the hemoglobin is delivered to a patient bloodstream in a substantially undegraded form. As used herein, the term "substantially undegraded form" means that at least 90% of the hemoglobin molecules retain the structure of comparable native hemoglobin.

In a first aspect of the presently claimed invention, an improved hemoglobin formulation forming a nanoparticle with improved zeta potential and encapsulation efficiency is provided. Said hemoglobin formulation in the first aspect of the presently claimed invention comprises hemoglobin-based oxygen carrier being embedded within a polyelectrolyte complex. The polyelectrolyte complex of the presently claimed invention is different from the previously claimed invention that the anionic polymer of the polyelectrolyte complex is algnite instead of the previously disclosed anionic polymers. The cationic polymer of the presently claimed invention is still chitosan but a higher concentration at about 0.1% w/v is used to enhance zeta potential and encapsulation efficiency of the nanoparticles when it is used in combination with algnite. The present nanoparticles formed from the improved hemoglobin formulation in the first aspect are prepared by a process which is similar to that for preparing the previously claimed nanoparticles via polyelectrolyte complexation, except that the concentration of various components in the hemoglobin formulation is different and there is an additional coating (re-coating) of high density chitosan on the hemoglobin-loaded chitosan-algnite nanoparticle in the presently claimed invention. In one embodiment of the process for making the nanoparticles of the presently claimed invention, the hemoglobin-based oxygen carrier is mixed with a solution comprising 0.05% w/v algnite in order to form a first mixture. Said first mixture is then added dropwise to an equal volume of oligo-chitosan at 0.05% w/v which is adjusted to pH 4.5 under stirring at room temperature until nanoparticles are formed and reaction stops. These hemoglobin-loaded chitosan-algnite nanoparticles are collected by centrifugation of the reaction mixture for certain period of time. A solution comprising a high density chitosan at 0.05 to 0.1% w/v is used to form an additional coating on the hemoglobin-loaded chitosan-algnite nanoparticles in order to regain its positive charge for enhancing electrostatic interaction of the nanoparticles with mucin in the gastrointestinal tract of a subject when said subject is orally administered with said nanoparticles. In one embodiment, the hemoglobin-loaded chitosan-algnite nanoparticles are added dropwise to a solution of high density chitosan under agitation such as by magnetic stiffing until said additional coating is formed.

In a second aspect of the presently claimed invention, an improved hemoglobin formulation for lyophilization to form a lyophilized hemoglobin solid mixture with low methemoglobin level is provided. Said hemoglobin formulation for lyophilization comprises one or more stabilizers and/or cryoprotectants. In one embodiment, said one or more stabilizers consist essentially of sucrose and hydroxypropyl-β-cyclodextrin (HPβCD). Said formulation further comprises one or more absorption enhancers. In another embodiment, said one or more absorption enhancers consist essentially of ethylene glycol tetraacetic acid (EGTA) and palmitoyl dimethyl ammonio propane sulfonate (PPS). Said formulation additionally comprises a protease inhibitor. In other embodiment, said protease inhibitor is soybean trypsin inhibitor (SBTI). Said formulation optionally comprises an antioxidant. In yet embodiment, e.g., N-acetyl cysteine or vitamin C, is used to either substitute sucrose as one of the stabilizers/cryoprotectants or optionally be an additional component in the hemoglobin formulation as an antioxidant.

DETAILED DESCRIPTION OF INVENTION

The present invention is directed to oral delivery formulations for HBOCs which deliver oxygen to the vasculature via oral administration. Three different categories of HBOCs for oral administration are described. Hemoglobin loads differently in each composition to create individualized and specific releasing and absorbing properties of the HBOC. In the compositions according to the present invention, the hemoglobin proteins are encapsulated in an acid-resistant material to avoid acid degradation in the stomach and enable absorption in the intestinal tract of a subject being administered with the compositions. The three pharmaceutical configurations are: (1) hemoglobin-loaded nanoparticles solution, (2) enteric-coated hemoglobin capsules and (3) enteric-coated hemoglobin tablets. A variety of hemoglobin is used in the pharmaceutical compositions including purified hemoglobin, cross-linked hemoglobin, non-polymeric tetrameric hemoglobin, polymeric hemoglobin, and conjugated hemoglobin of various molecular weights. Examples of hemoglobin that can be used in the oral pharmaceutical compositions of the present invention are set forth in U.S. Pat. Nos. 7,932,356, 7,989,593, 8,048,856, 8,084,581, 8,106,011, the disclosures of which are incorporated by reference herein.

In the hemoglobin-loaded nanoparticle solution, hemoglobin is embedded within a polyelectrolyte complex, comprised of anionic polymer and cationic chitosan chains to ensure the intact structure of hemoglobin and enabling efficient absorption via the oral administration route. Anionic polymers that could complex with chitosan include poly(methacrylic acid)-poly(methyl methacrylate) (PMAA-PMMA) copolymer, hydroxyl propylmethylcellulose phthalate (HPMCP) and gamma-glutamic acid (γ-PGA). The proportion of anionic and cationic components are maintained at ratio at which positively charged nanoparticles are produced, which is found to have enhanced mucosal adhesion to the negatively charged intestinal epithelial (Dünnhaupt et al., 2011).

Chitosan, a cationic polysaccharide, is derived from chitin by alkaline deacetylation. The polysaccharide chain is constituted by N-glucosamine and N-acetyl glucosamine units. Chitosan is non-toxic and soft tissue compatible (Iwasaki et al., 2004). More importantly, chitosan has a special property of adhering to the mucosal surface and transiently opening the tight junctions between epithelial cells (Artursson et al., 1994), making it an ideal intestinal absorption enhancer.

Figure 1:
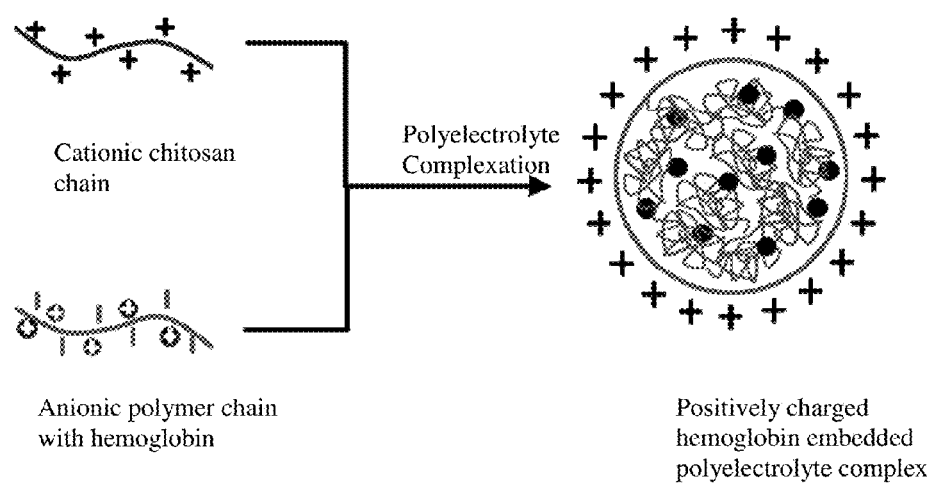
FIG. 1 shows the formation and structure of a hemoglobin loaded nanoparticle.

Hemoglobin-loaded nanoparticles are produced via polyelectrolyte complexation under an aqueous-based condition at room temperature without using harmful organic solvents that would disrupt the intact structure of hemoglobin. The nanoparticles include three major components: anionic polymer, chitosan, and hemoglobin. FIG. 1 illustrates the complexation process of the cationic chitosan chains, pre-mixed anionic polymer chains and hemoglobin, which thereby producing the final product of a positively charged hemoglobin-loaded nanoparticle. The pre-mixed solution of anionic polymer and hemoglobin is adjusted to a final pH that is above the isoelectric point of hemoglobin, inducing a positive charge on the protein surface, hence a strong affinity with the anionic polymer. Exemplary methods for forming the nanoparticles are disclosed in Makholf et al., 2011, Sonaje et al., 2010, Lin et al., 2008, Brunel et al., 2010, the disclosures of which are incorporated by reference.

It has been demonstrated that chitosan exhibit antibacterial activity against *Escherichia coli*, and therefore no preservative is needed for long term storage (Sudarshan et al., 1992). However, to prolong shelf-life of the pharmaceutical compositions, vitamin C or N-acetyl cysteine (NAC) is optionally added to the nanoparticle mixture. Vitamin C or N-acetyl cysteine acts as antioxidant to prevent the formation of inactive met-hemoglobin which cannot deliver oxygen. Inactive ingredients (excipients) optionally include coloring, flavoring, desiccants, further coatings for facilitating swallowing of the oral compositions, etc.

Figure 4:
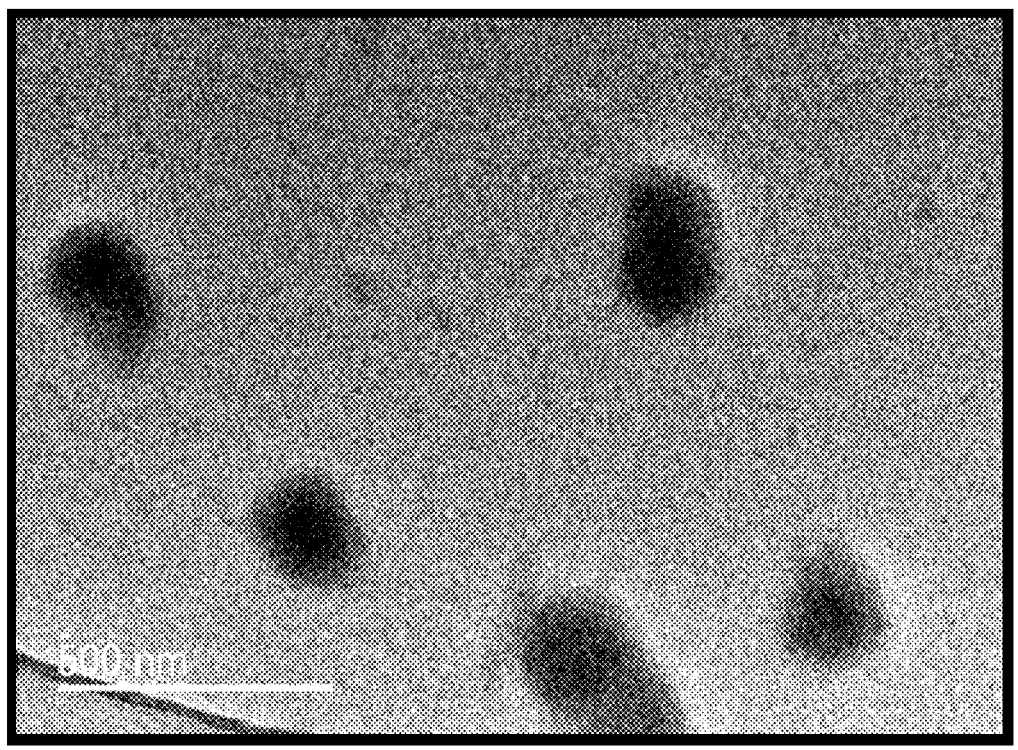
FIG. 4 shows the transmission electron microscope image of hemoglobin loaded nanoparticles.

In one embodiment, 50 mL of 0.05% w/v PMAA-PMMA copolymer aqueous solution is prepared and adjusted to pH 7. Hemoglobin (200 mg) is added to the prepared PMAA-PMMA copolymer solution and mixed well to form a first mixture. Same volume (50 mL) of 0.05% w/v chitosan (molecular weight: 130 k) aqueous solution is prepared and adjusted to pH 4.5. The first mixture is then added dropwise to the pH-adjusted chitosan solution under magnetic stirring at room temperature. Nanoparticles are collected by ultracentrifugation at 20,000 rpm for 1 hour. The pellet containing a plurality of nanoparticles after ultracentrifugation is re-suspended in 5 mL of deionized water for further characterization. Particle size and zeta potential are measured using dynamic light scattering and laser Doppler electrophoresis (Zetasizer HS3000, Malvern), the results of which are presented in Table 1. Highly positively charged (41 mV) hemoglobin-loaded nanoparticles with a particle size of about 574 nm is produced. Loading of hemoglobin into the polyelectrolyte complex increases both the particle size and zeta potential compared to the blank nanoparticles prepared by the same procedures. Spherical morphology of hemoglobin-loaded nanoparticles is also shown in FIG. 4 obtained by the transmission electron microscope (JEM-2011, JEOL). The encapsulation/association efficiency percentage (AE %) and final product concentration are presented in Table 1. The quantity of hemoglobin is measured and determined by a HPLC-UV system (Waters 1525, Waters) at a wavelength of about 410 nm. The column used is a silica-based gel filtration column (BioSep-SEC-S 2000 SEC, 300×7.8 mm, Phenomenex). Flow rate and injection volume are 25 mL/min and 30 μL respectively. AE % is calculated by the following equation:

$$AE\% = \frac{\text{total amount of hemoglobin} - \text{free hemoglobin in supernatant}}{\text{total amount of hemoglobin}} \times 100$$

TABLE 1

The encapsulation/association efficiency percentage (AE %) and hemoglobin concentration of nanoparticles

| Sample | Particle Size [nm] | Zeta Potential [mV] | Encapsulation/ Association Efficiency [%] | Product Hemoglobin Concentration [mg/mL] |
|---|---|---|---|---|
| Blank nanoparticle | 369 | 28 | — | — |
| Hemoglobin-loaded nanoparticle | 574 | 41 | 28.7 | 7.8 |

In the presently claimed invention, an improved hemoglobin formulation is provided to form a hemoglobin-loaded nanoparticle with an improved properties such as zeta potential and encapsulation or association efficiency. In one embodiment of the presently claimed invention, 10 mL of 0.1% w/v alginate solution (negatively charged) is mixed well with hemoglobin (20 mg) to form a first mixture. 10 mL of 0.05% w/v oligo-chitosan (positively charged) is prepared and adjusted to pH 4.5. The first mixture is then added drop-wise to the pH-adjusted oligo-chitosan solution under magnetic stiffing (700 rpm) at room temperature. Nanoparticles are collected after ultracentrifugation (12,000 g) for 20 minutes until nanoparticles are formed and reaction stops. The pellet is re-suspended in 1 mL of deionized water for measuring the particle size and zeta potential. The amount of encapsulated hemoglobin released in PBS (pH 6.8) is also measured. The result is summarized in Table 2. The size of the nanoparticles is in the suitable range with high encapsulation efficiency. Since positively charged hemoglobin-loaded nanoparticles can interact with negatively charged residues of mucin in the intestine by electrostatic interactions more efficiently, the uptake of the loaded hemoglobin in the gastrointestinal track is increased. Therefore, the negatively charged chitosan-algnite hemoglobin-loaded nanoparticles obtained from Table 2 are further re-coated with 0.05% and 0.1% w/v high-density chitosan (positively charged) ("CSHD"), respectively, to regain its positive charge (Table 3), hence increases its electrostatic interaction with mucin in the intestine. The results in Table 3 show that the hemoglobin-loaded chitosan-algnite nanoparticles re-coated with 0.1% w/v CSHD results in higher zeta potential. However, the hemoglobin-loaded chitosan-algnite nanoparticles re-coated with 0.05% w/v CSHD results in higher encapsulation/association efficiency. Overall, the nanoparticles formed from the improved hemoglobin formulation of the presently claimed invention has a higher encapsulation/association efficiency than that formed from the previously claimed hemoglobin formulation. Using a higher concentration of high-density chitosan (e.g. 0.1% w/v) in combination with alignate instead of other negatively charged polymer such as PMAA-PMAA co-polymer can significantly enhance the zeta potential and encapsulation efficiency of the hemoglobin in the nanoparticles in order to achieve a controlled-release profile of the hemoglobin at the target site (i.e. intestinal tract) via oral administration.

TABLE 2

Characteristic determination of chitosan-alginate nanoparticles before re-coating

| Oligo-chitosan (w/v) | Alginate (w/v) | pH | Amount of hemoglobin loading (mg) | Particle size (nm) | Zeta potential (mV) | Encapsulation efficiency (%) | Amount of hemoglobin released in PBS (mg) |
|---|---|---|---|---|---|---|---|
| 0.05% | 0.1% | 4.5 | 20 | 690 | −40.6 | 89.22 | 9.792 |

TABLE 3

Characteristic determination of chitosan-alginate nanoparticles after re-coating

| Re-coat polymer: CSHD (w/v) | Particle size (nm) Before recoat | Particle size (nm) After recoat | Zeta potential (mV) Before recoat | Zeta potential (mV) After recoat | Encapsulation efficiency (%) | Amount of hemoglobin released in PBS (mg) |
|---|---|---|---|---|---|---|
| 0.05% | 3,102 | 12,317 | −59.8 | +21.67 | 86.53 | 1.079 |
| 0.1% | | 9,420 | | +54.6 | 67.47 | 1.136 |

Lyophilization is a well-established technique to create stabilized dry protein formulations. The method of the present invention describes hemoglobin formulations prepared by lyophilization with the addition of different cryoprotectants and intestinal absorption enhancers before fabricating into enteric-coated capsules or tablets. Cryoprotectants such as glucose, sucrose or trehalose are added to the hemoglobin solution to preserve the structure of protein during lyophilization. Intestinal absorption enhancers such as polyoxyethylene-20-sorbitan monooleate, poly(ethylene oxide)-poly(propylene oxide)-poly(ethylene oxide) tri-block copolymer, cyclodextrin, oleic acid, sodium decanoate, sodium octanoate, sodium deoxycholate and sodium cholate hydrate are included in the lyophilization formulations. Other stabilizers for the hemoglobin may also be included such as antioxidant.

In an embodiment, six lyophilization formulations (Table 4) are tested using a laboratory freeze dryer (LYOBETA 25, Telstar) under operating parameters listed in Table 5. Sucrose is added as a cryoprotectant and N-acetyl cysteine as an antioxidant. Two non-ionic surfactants are added to the hemoglobin solution as a stabilizer and intestinal absorption enhancer. Both polyoxyethylene-20-sorbitan monooleate (commonly known as Polysorbate 80) and poly(ethylene oxide)-poly(propylene oxide)-poly(ethylene oxide) tri-block copolymer (commonly known as Polyethylene-polypropylene glycol, PPG) are FDA approved excipients for oral formulations. PPG is a triblock copolymer with a PEO-PPO-PEO weight ratio of 40%-%-40% and a molecular weight of 8,400 Da. Met-hemoglobin level is measured before and after lyophilization. The lyophilized samples are reconstituted in deionized water before met-hemoglobin measurement using a blood gas analyzer (IL 682 Co-Oximeter System, Instrumental Laboratory). There is no significant change in met-hemoglobin level after lyophilization. The group with PPG (Formulation Samples F3, F6; shown in Table 4) has the lowest met-hemoglobin level compared to the other formulations without PPG.

using a laboratory freeze dryer (LYOBETA 25, Telstar) under operating parameters listed in Table 5. In this embodiment, surcose and hydroxypropyl-β-cyclodextrin (HPβCD) are added as stabilizers and/or cyroprotectants, while N-acetyl cysteine can be optionally added as an alternative to sucrose, which is also an antioxidant. HPβCD is a cyclic oligosaccharide with 7-membered sugar ring molecule. This molecule is approved by FDA as an oral drug stabilizer, and is commonly used in pharmaceutical applications for drug delivery. Its spatial arrangement of toroid structure (hydrophobic inside and hydrophilic outside) allows it to penetrate body tissues and forms complexes with hydrophobic pharmaceutical active ingredients. Thus this stabilizer enhances the solubility and bioavailability of the active ingredients (Becket et al., 1999). Ethylene glycol tetraacetic acid (EGTA) and palmitoyl dimethyl ammonio propane sulfonate (PPS) are added as absorption enhancer. These absorption enhancers facilitate the transport of hemoglobin across the epithelial membrane by modifying the epithelial intercellular tight junctions (Gupta et al., 2013). In order to minimize the enzymatic degradation of hemoglobin in the gastrointestinal tract by trypsin and chymotrypsin, a protease

TABLE 4

Met-hemoglobin measurement of six hemoglobin lyophilization formulations

| Sample | Hemoglobin [mg/mL] | Sucrose [M] | NAC [w/v %] | Polysorbate 80 [mM] | PPG [w/v %] | Met-Hb [%] before lyophilization | Met-Hb [%] After lyophilization |
|---|---|---|---|---|---|---|---|
| F1 | 5 | 0.25 | 0 | 0 | 0 | 6.3 | 6.9 |
| F2 | 5 | 0.25 | 0 | 3 | 0 | 6.3 | 7.7 |
| F3 | 5 | 0.25 | 0 | 0 | 0.2 | 6.3 | 6.5 |
| F4 | 5 | 0.25 | 0.2 | 0 | 0 | 6.3 | 7.0 |
| F5 | 5 | 0.25 | 0.2 | 3 | 0 | 6.3 | 7.2 |
| F6 | 5 | 0.25 | 0.2 | 0 | 0.2 | 6.3 | 6.5 |

TABLE 5

Operating parameters of laboratory freeze dryer (LYOBETA 25, Telstar)

| Step | Process | Temp [° C.] | Vacuum [mbar] | Time [hr] |
|---|---|---|---|---|
| 1 | Freezing | −60 | — | 2 |
| 2 | Freezing | −60 | — | 6 |
| 3 | Chamber Vacuum | −60 | 0.5 | 2 |
| 4 | Primary drying | −10 | 0.5 | 2 |
| 5 | Primary drying | −10 | 0.5 | 10 |
| 6 | Primary drying | 0 | 0.5 | 1 |
| 7 | Primary drying | 0 | 0.5 | 8 |
| 8 | Secondary drying | 15 | 0.2 | 1.5 |
| 9 | Secondary drying | 15 | 0.08 | 8 |
| 10 | Secondary drying | 25 | 0.08 | 1 |
| 11 | Secondary drying | 25 | 0.001 | 6 |

In an embodiment of the presently claimed invention, an improved lyophilized formulation (F7) (Table 6) is tested inhibitor, soybean trypsin inhibitor (SBTI) is added to the hemoglobin solution (Yamamoto et al., 1994). With the addition of these stabilizers and absorption enhancers, the met-hemoglobin level after lyophilization of this formulation does not increase to a high level (≥8%) (Table 6). As compared to lyophilized hemoglobin formed from F1 to F6 formulations as previously provided in Table 4, the lyophilized hemoglobin formed from formulation F7 has the lowest met-hemoglobin level after lyophilization among the seven formulations. This result reveals that the addition of these stabilizers, absorption enhancers and protease inhibitor into hemoglobin formulation F7 further improves at least the stability of the hemoglobin molecule during lyophilization and even after lyophilization. The stability effect by adding HPβCD into the formulation F7 is even better than those prior formulations with PPG (e.g. F3 and F6).

TABLE 6

Met-hemoglobin measurement of an improved lyophilized hemoglobin formulation

| Formulation | Hemoglobin (mg/mL) | Sucrose (%, w/v) | HPβCD (%, w/v) | EGTA (mg/mL) | PPS (mg/mL) | SBTI (mg/mL) | Met-Hb (%) after lyophilization |
|---|---|---|---|---|---|---|---|
| F7 | 300 | 6 | 4 | 70 | 4.5 | 25 | 6.3 |

To investigate the trans-epithelial transport of the lyophilized hemoglobin (Formulation Samples F1-F3; shown in Table 4), in vitro, Caco-2 cell monolayers on trans-well setup is used. Before the start of the experiment, the cell monolayers are washed and incubated with pre-warmed Hank's balanced salt solution (HBSS), supplemented with NaHCO$_3$ (0.35 g/L) and 25 mM HEPES (if pH 6.5) or 10 mM methanesulfonic acid (if pH<6), for 30 min. HBSS are aspirated and refilled 1.5 ml HBSS to apical compartment and 2 ml to basolateral compartment. HBOCs and excipients are loaded into the apical compartment. FITC-dextran (4 kDa, Sigma) could be used as a positive maker to test the permeability of the cell monolayer. The initial TEER values were measured by Millicell-ERS. The cells are incubated at 37° C. with orbital shaking at 50 r.p.m. for 3 hours. TEER values are recorded at the time point of 1.5 and 3 hours. At the end of the experiment, 2 ml of HBSS at the basolateral compartment are collected and analyzed with high-performance liquid chromatography (HPLC) to quantify the pass-through HBOC. FITC-dextran is quantified using fluorescence spectrometer (EUROStar). Hemoglobin absorption percentage and the change in TEER at the end of the experiment are presented in Table 7. Absorption percentage is calculated as the amount of hemoglobin in the basolateral compartment at the end of the study compared to the initially loaded hemoglobin amount in the apical compartment. A 3.9-fold and 2.6-fold increase in hemoglobin absorption is induced by the addition of Polysorbate 80 and PPG respectively. The presence of Polysorbate 80 in sample F2 induces a more significant drop (10%) of TEER compared to sample F1, whereas there is no significant change in TEER for sample F3.

TABLE 7

Hemoglobin absorption percentage and the change in TEER of lyophilized hemoglobin formulations (F1-F3)

| Samples | Absorption % | % of initial TEER |
| --- | --- | --- |
| FITC-dextran | 5.6 | 91.8 |
| F1 (hemoglobin 10 mg) | 1.7 | 87.0 |
| F2 (hemoglobin 10 mg + Polysorbate 80 3 mM) | 6.6 | 76.8 |
| F3 (hemoglobin 10 mg + PPG 0.2%) | 4.4 | 97.1 |

Figure 5A:
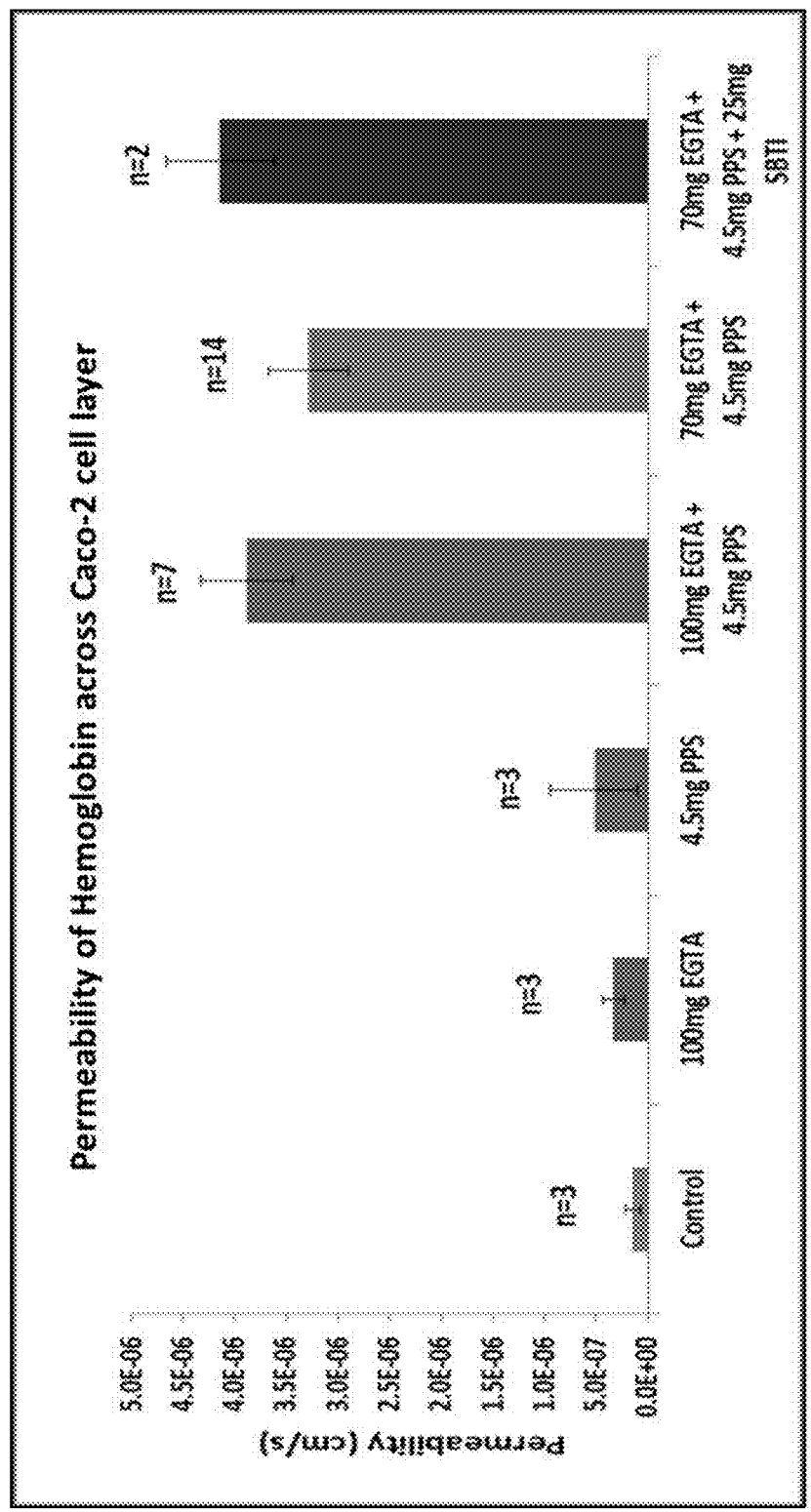
FIG. 5 shows the results of permeability (A) and TEER percentage change during and after absorption (B) of the lyophilized hemoglobin formulation F7 across Caco-2 cell layer as compared to other samples—
Figure 5B:
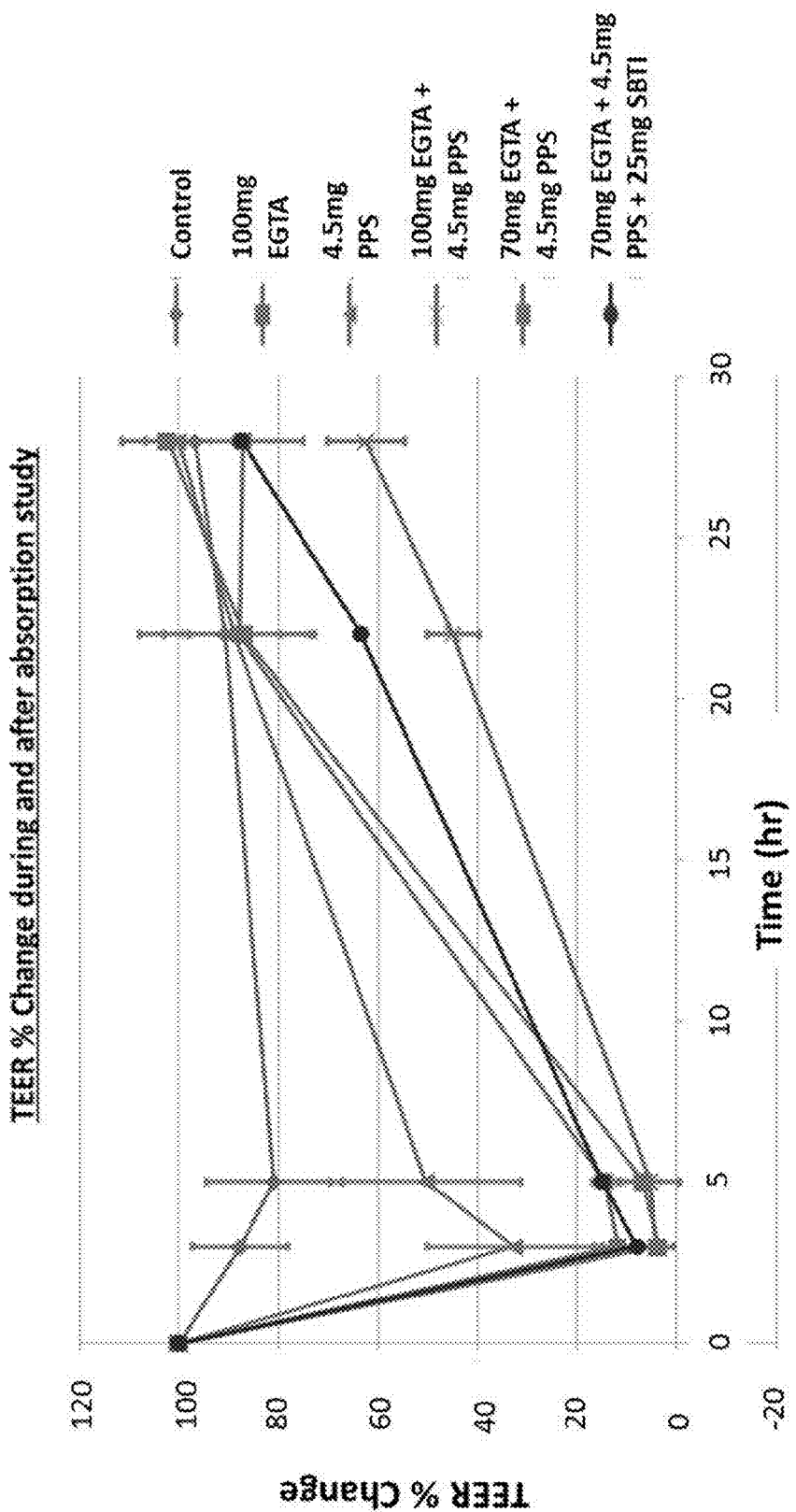

The hemoglobin permeability and the change in TEER of lyophilized hemoglobin formulation F7 prepared according to Table 6 (containing 70 mg/mL EGTA, 4.5 mg/mL PPS, 25 mg/mL SBTI) are presented in FIGS. 5A and 5B, respectively. In FIG. 5A, it is shown that 100 mg EGTA and 4.5 mg PPS individually enhances the permeability of hemoglobin across Caco-2 cells layer by 2.2-fold and 3.0-fold respectively. The lyophilized formulation F7 shows synergetic effect on permeability which is increased by 28-fold. Percentage change of TEER in FIG. 5B shows that the TEER of F7 (70 mg/mL EGTA, 4.5 mg/mL PPS, 25 mg/mL SBTI) rebounds to 80% after 24 hours. F7 appears to be non-invasive to Caco-2 cells.

Figure 6:
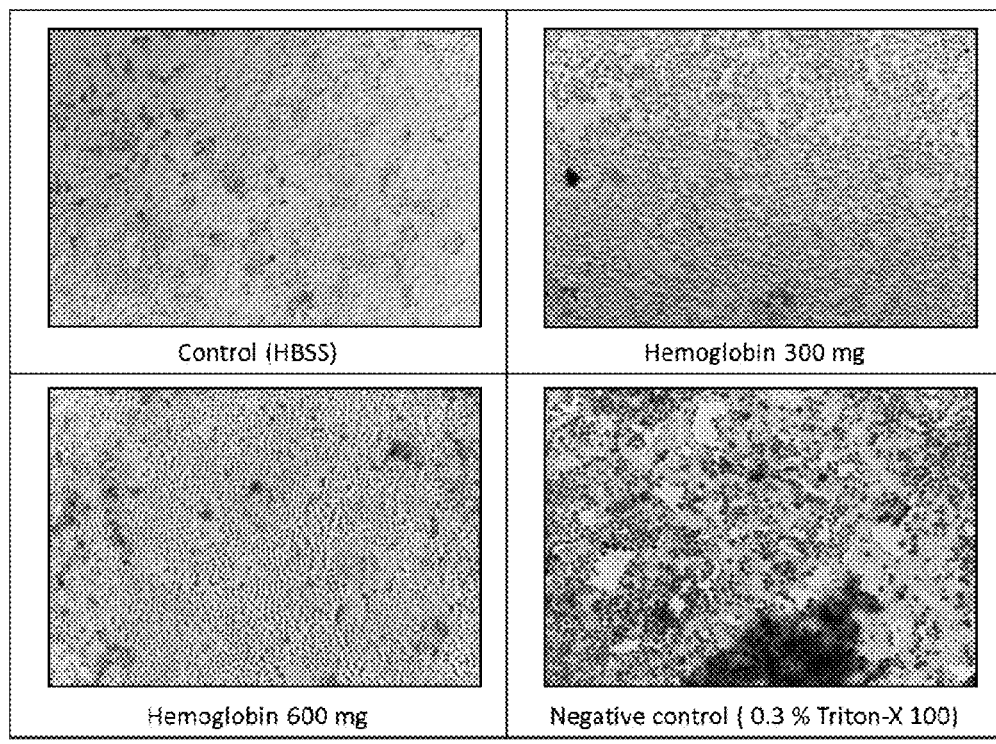
FIG. 6 Cytotoxicity of the lyophilized hemoglobin formulation F7 on Caco-2 cell.

MTT experiments are carried out to confirm the toxicity of the lyophilized hemoglobin (10 mg of the lyophilized formulation F7) by using Caco-2 cells model. Caco-2 cells are cultured as mentioned above, followed by seeding 1×10$^4$ cells on each well of 96-well culture plate. Cells are incubated with different dosages of the lyophilized hemoglobin formulation F7 (300 mg and 600 mg) for 3 hours at 37° C. (FIG. 6). The negative control is performed by using 0.1% Triton X-100. There is no significant difference on viability of the control group (medium only) compared to the Caco-2 cells treated with hemoglobin (300 mg and 600 mg) F7 formulation (70 mg/mL EGTA, 4.5 mg/mL PPS, 25 mg/mL SBTI). It indicates that no cytotoxic effect of this lyophilized hemoglobin formulation with EGTA and PPS to the cells. However, significant cell death is observed in the negative control group (0.1% Triton X-100).

Figure 2:
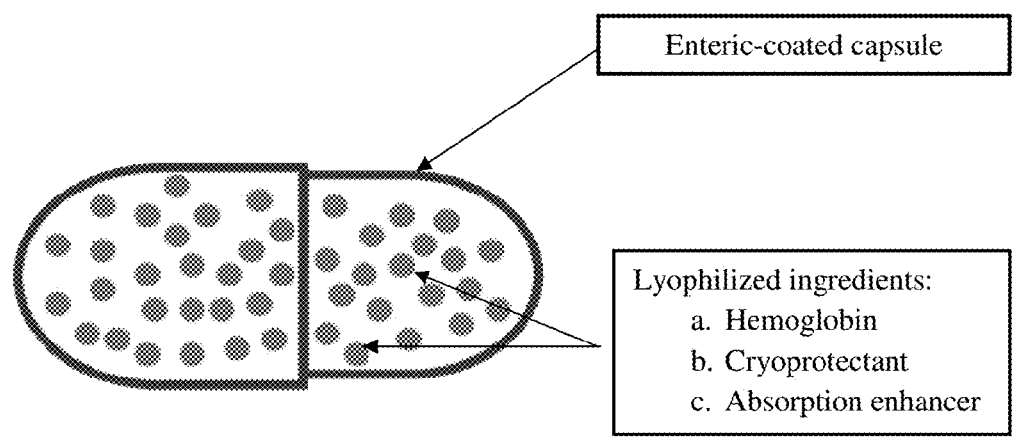
FIG. 2 shows the structure of enteric-coated hemoglobin capsule.
Figure 7:
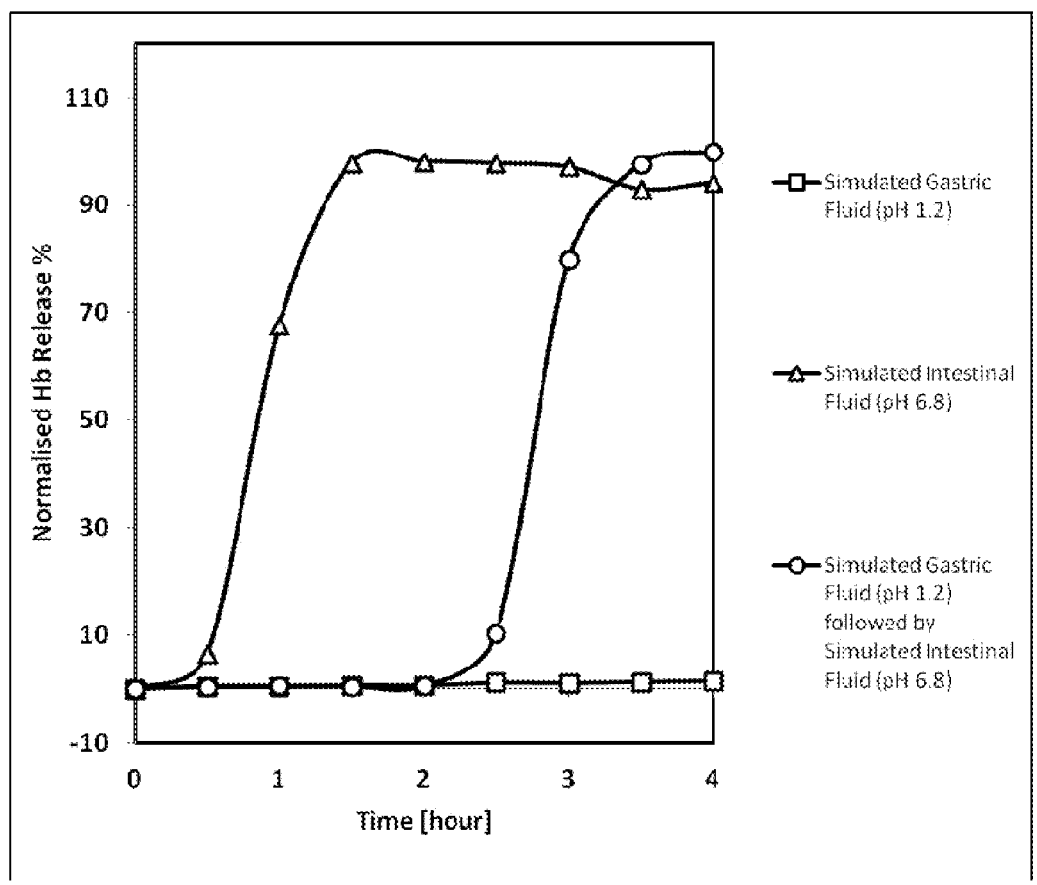
FIG. 7 Dissolution profiles of encapsulated lyophilized hemoglobin capsules.

In one embodiment, lyophilized hemoglobin solid (can be in powder or particle form) of formulation F7 is encapsulated in enteric-coated capsules. Enteric-coated capsules are commercially available and are composed of gelatin with a polyacrylic resin coating. Enteric-coated capsule is acid-resistant but dissolves at pH levels of the order of 6-7 which is the pH level found in the intestines. FIG. 2 is a schematic diagram showing the basic structure of the enteric-coated capsule of the present invention. Dissoulution study of enteric-coated hemoglobin capsules is performed in simulated gastric fluid (pH 1.2, without pepsin) and simulated intestinal fluid (pH 6.8, without pancreatin) at 37° C. Three enteric-coated capsules (size 9) are each filled with 10 mg of lyophilized hemoglobin solid mixture. Each capsule is placed into 10 mL of release medium in three scenarios: (1) simulated gastric fluid for 4 hours; (2) simulated intestinal fluid for 4 hours; (3) simulated gastric fluid for 2 hours followed by simulated intestinal fluid for 2 hours. Amount of hemoglobin released at different sampling time is determined by HPLC-UV measurement at 410 nm. The dissolution profiles of the three scenarios are shown in FIG. 7. Hemoglobin is well-protected by the enteric-coated capsule in simulated gastric fluid and no hemoglobin is released in scenario 1. Hemoglobin is only released when placed in the simulated intestinal fluid in scenario 2 and 3.

In one embodiment, an in vivo study of the lyophilized hemoglobin F7 is performed to evaluate the efficacy of systemic delivery of hemoglobin. Sprague Dawley (SD) rats (about 300 g, n=3) are subjected to oral administration of the lyophilized hemoglobin encapsulated in enteric coated capsule containing 9 mg of powder. Capsules are given to each rat with a feeding tube at a dose of 0.9 g/kg. Blood is collected from the tail vein to determine the plasma hemoglobin concentration using a hemoglobin analyzer (HemoCue® Plasma/Low Hb System). Plasma hemoglobin concentrations are measured before feeding and at time intervals of 3 and 6 hours post-feeding. Baseline plasma hemoglobin concentration is 0.17 g/dL and progressive increases over the study period of 6 hours. Plasma hemoglobin concentrations are 0.28 g/dL and 0.34 g/dL at 3 and 6 hour interval respectively, which accounted for 63.5% and 97.1% increase compared to baseline.

In one embodiment, the efficacy of the treatment of anemia by oral delivery of hemoglobin is studied by a hemorrhagic anemia animal model. Male adult Wistar rats with a mean body weight of 200-250 g are used in the study. The hemorrhagic anemia model is established by 30% blood phlebotomy, in which 15% of blood is removed on Day 1 followed by another 15% on Day 3. After each blood withdrawal, equal volume of saline solution is infused into the animal. Pressure is applied for hemostasis after wound closure, and antibiotics were given intramuscularly. Hemoglobin level is determined on Day 4 to confirm the establishment of the hemorrhagic anemia model (HGB<10 g/dL). The anemic rats are randomly divided into two groups, saline control group (n=6) and hemoglobin group (n=8). Lyophilized hemoglobin powder is reconstituted in saline solution to a concentration of 0.2 g/mL and is administered to the animal by oral gavage at a dose of 1 g/kg. The same volume (5 mL) of hemoglobin solution or saline solution is administrated to the animal orally twice a day, i.e. morning and evening with an interval of 8 hours. Blood parameters and body weight, including hemoglobin content (HGB, in Table 8), hematocrit (HCT, in Table 9), red blood cell count (RBC, in Table 10), mean corpuscular volume (MCV, in Table 11) and body weight (BW, in Table 12), are measured on day 7 and day 14 post-dosing. All data are presented as mean±standard deviation. T-TEST is used for statistical analysis. Values of p<0.05 are considered significant. It is found that there is a significant increase in HCT, RBC, MCV and BW on post-dose day 7 compared to the baseline value before blood withdrawal. Significant improvement in hemoglobin content (HGB), hematocrit (HCT), red blood cell count (RBC) and mean corpuscular volume (MCV) and maintaining body weight (BW) without adverse effect compared to the saline control group are also observed.

TABLE 8

Change in hemoglobin level (HGB, g/L)

| | Before Blood Withdrawal | After Blood Withdrawal | Post-dose Day 7 | Post-dose Day 14 |
|---|---|---|---|---|
| Saline Group (Control) | 124.43 ± 7.43 | 75.29 ± 5.31$^{++}$ | 119.77 ± 7.76 | 119.57 ± 7.74 |
| Hemoglobin group | 128.13 ± 6.50 | 72.63 ± 4.04$^{++}$ | 135.5 ± 5.48** | 130.71 ± 8.80 |

$^{++}$p < 0.01, compare with baseline value before blood withdrawal
**p < 0.01, compare with saline group value

TABLE 9

Change in hematocrit (%, HCT)

| | Before Blood Withdrawal | After Blood Withdrawal | Post-dose Day 7 | Post-dose Day 14 |
|---|---|---|---|---|
| Saline Group (Control) | 38.91 ± 1.92 | 24.06 ± 1.55$^{++}$ | 34.91 ± 0.96$^{++}$ | 38.07 ± 1.96 |
| Hemoglobin Group | 37.49 ± 2.36 | 23.16 ± 1.27$^{++}$ | 39.81 ± 1.10$^{+}$,** | 40.31 ± 1.70$^{+}$ |

$^{+}$p < 0.05, $^{++}$p < 0.01, compare with baseline value before blood withdrawal
**P < 0.01, compare with saline group

TABLE 10

Change in red blood cell count (1 × 10$^{12}$/L, RBC)

| | Before Blood Withdrawal | After Blood Withdrawal | Post-dose Day 7 | Post-dose Day 14 |
|---|---|---|---|---|
| Saline Group | 6.82 ± 0.33 | 4.03 ± 0.30$^{++}$ | 5.68 ± 0.14$^{++}$ | 5.95 ± 0.42$^{++}$ |
| Hemoglobin Group | 6.56 ± 0.42 | 3.85 ± 0.19$^{++}$ | 6.08 ± 0.45* | 6.12 ± 0.58 |

$^{++}$P < 0.01, compare with baseline value before blood withdrawal
*P < 0.05, compare with saline group

TABLE 11

Change in mean corpuscular volume (fL, MCV)

| | Before Blood Withdrawal | After Blood Withdrawal | Post-dose Day 7 | Post-dose Day 14 |
|---|---|---|---|---|
| Saline Group (Control) | 57.06 ± 1.07 | 59.76 ± 1.50$^{+}$ | 64.10 ± 1.14$^{++}$ | 64.10 ± 1.73$^{++}$ |
| Hemoglobin Group | 57.15 ± 0.99 | 60.19 ± 0.97$^{++}$ | 65.70 ± 1.12$^{++}$,* | 66.40 ± 5.20$^{++}$ |

$^{++}$P < 0.01, compare with baseline value before blood withdrawal
*P < 0.05, compare with saline group

TABLE 12

| | Change in rat body weight (g, BW) | | | |
|---|---|---|---|---|
| | Before Blood Withdrawal | After Blood Withdrawal | Post-dose Day 7 | Post-dose Day 14 |
| Saline Group (Control) | 256.29 ± 4.46 | 240.86 ± 4.01++ | 244.71 ± 8.64+ | 254.71 ± 11.45 |
| Hemoglobin Group | 258.00 ± 8.87 | 255.75 ± 8.43** | 258.33 ± 9.03* | 260.25 ± 11.94 |

Figure 8:
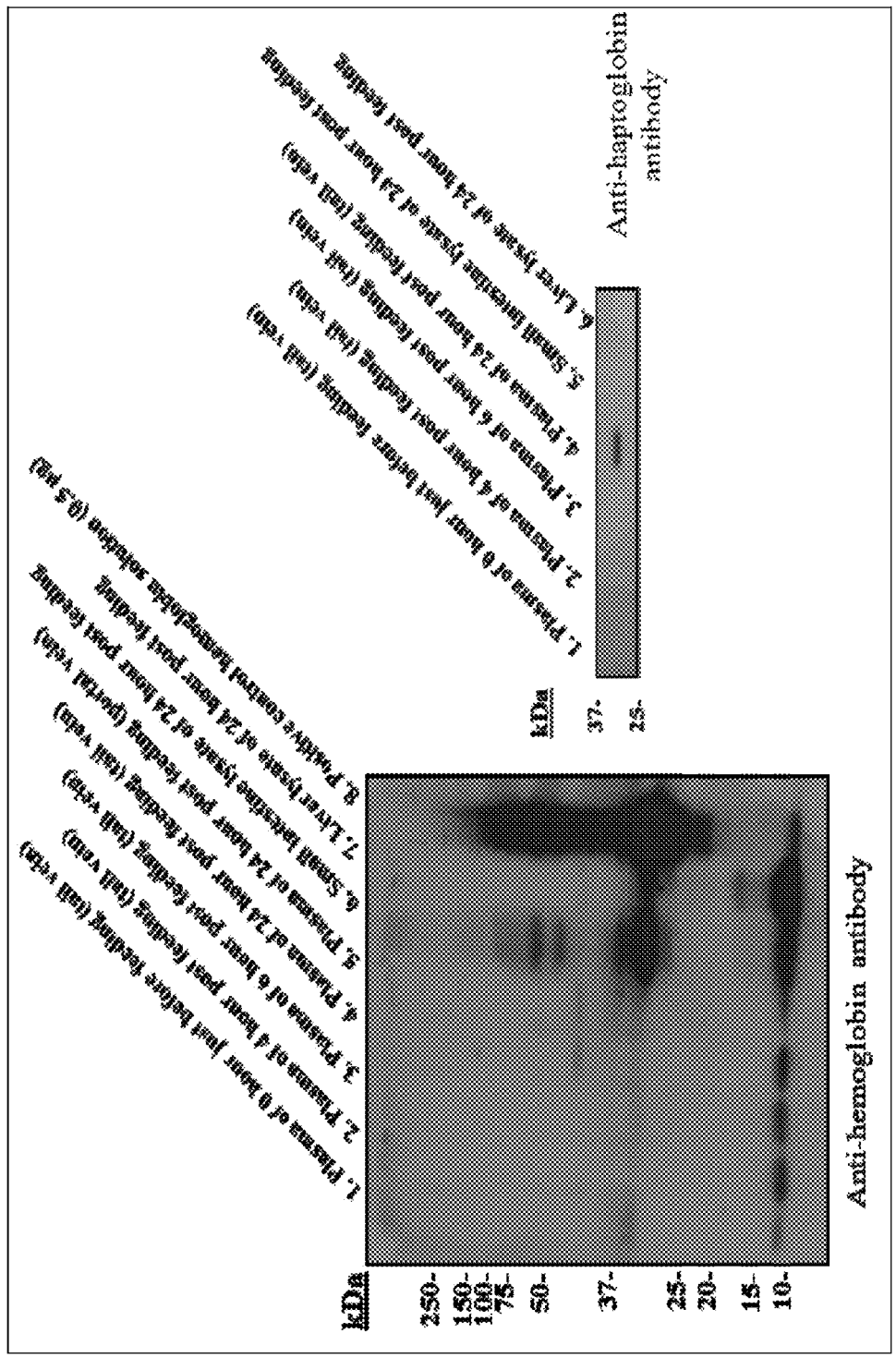
FIG. 8 Western blot images of hemoglobin detection from plasma samples after oral dosing of the lyophilized hemoglobin capsules F7 in rats.

++P < 0.01, compare with baseline
*P < 0.05, P < 0.01 compare with saline group In one embodiment, an in vivo study of the lyophilized hemoglobin formulation F7 encapsulated in capsules (70 mg/mL EGTA, 4.5 mg/mL PPS, 25 mg/mL SBTI, 4% w/v HPβCD, 6% w/v sucrose) is performed to evaluate the efficacy of systemic delivery of hemoglobin. Sprague Dawley (SD) rats (about 300 g) are subjected to oral administration of the lyophilized hemoglobin encapsulated in an enteric coated capsule containing 10 mg of lyophilized hemoglobin powder. Capsules are given to each rat with a feeding tube at a dose of 0.2 g/kg. Tail vein blood samples are collected at each time point (0, 4, 6 and 24 hours), and portal vein blood samples are collected from the pentobarbital-anesthetized rat. Plasma samples are separated from the blood samples after centrifugation. Organ/tissue lysates are homogenized from small intestines and livers that are dissected from the sacrificed rats. Hemoglobin and haptoglobin is detected from the plasma and lysate samples by Western Blot protein analysis method (FIG. 8**). Hemoglobin protein is only detected in small intestine lysate, but not plasma samples of each time point after oral dosing of the lyophilized hemoglobin capsules. Nevertheless, haptoglobin protein is up-regulated in the plasma sample after 24 hours post oral administration.

Figure 9:
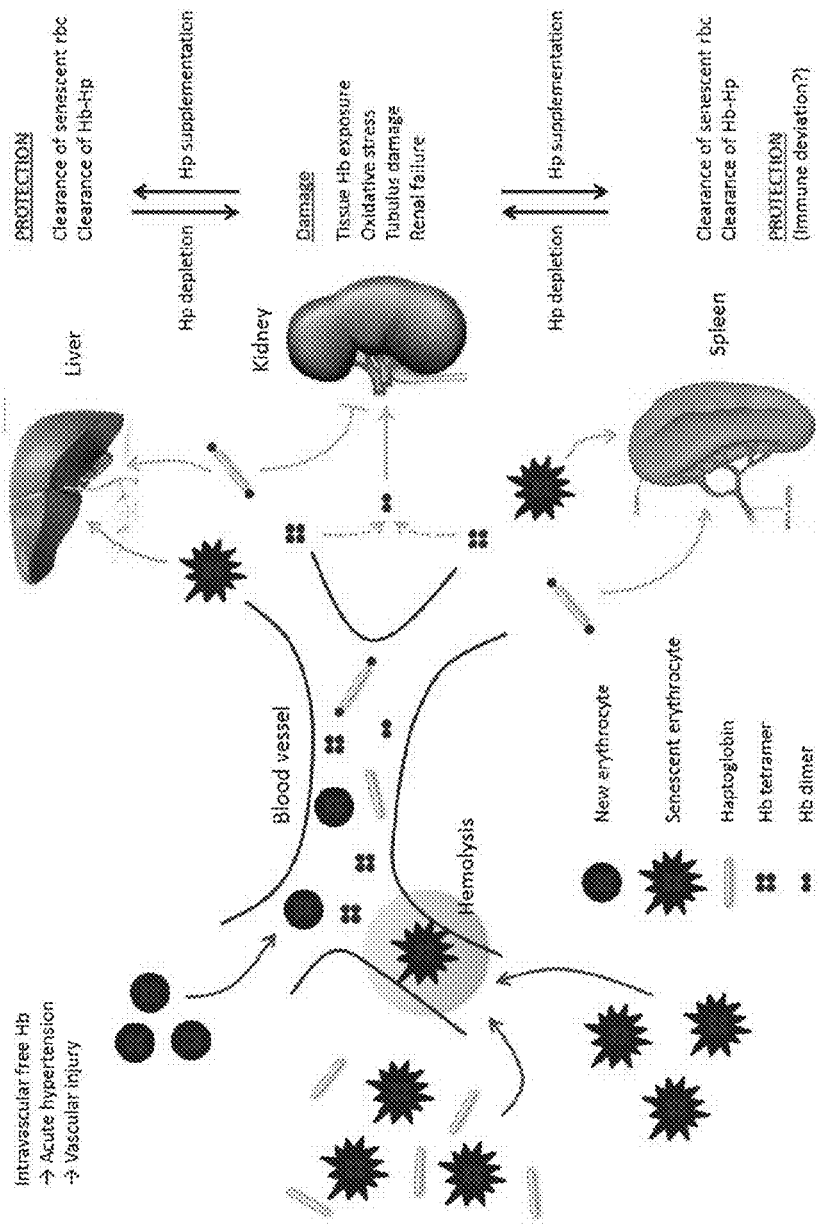
FIG. 9 Systemic flow of physiological mechanism of haptoglobin and hemoglobin binding.

It is well-known that haptoglobin expression is induced in liver by free hemoglobin, thus resulting in an increased amount of haptoglobin in blood plasma. Haptoglobin binds to free hemoglobin with extremely high affinity with $K_d \sim 1 \times 10^{-15}$ mol/L. Hemoglobin-haptoglobin complex is eliminated by macrophages of liver. The elimination of hemoglobin is hypothesized to be a physiological protective mechanism against an excess supply of oxygen (hypoxia) in an organism (Baek et al., 2012). A systemic flow of physiological mechanism of haptoglobin and hemoglobin binding is presented in FIG. 9.

Figure 10:
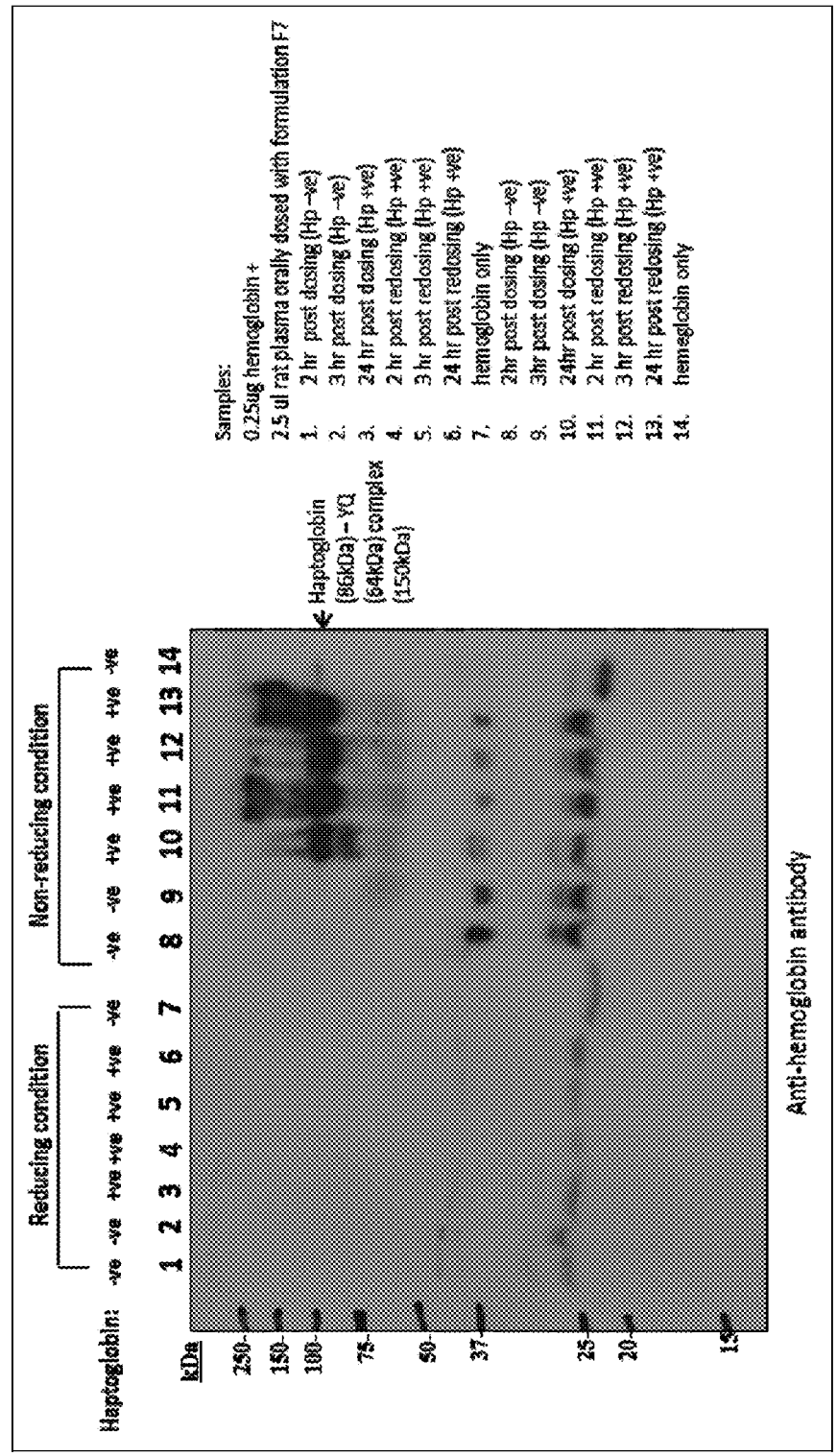
FIG. 10 SDS-PAGE images of haptoglobin-hemoglobin complex in plasma samples.

In one embodiment, the interaction of hemoglobin and haptoglobin is studied by incubating plasma samples collected from a rat 30 minutes after being orally administered with the lyophilized formulation F7. Some of the plasma samples have shown the presence of haptoglobin. Samples are run in SDS-PAGE under reducing and native conditions and the images are shown in FIG. 10. Bands of haptoglobin-hemoglobin complex are detected in samples with haptoglobin in a non-reducing condition. These findings confirm the in vivo interaction/binding between haptoglobin and free hemoglobin in the present animal model after being administered with said lyophilized hemoglobin formulation F7.

Figure 11:
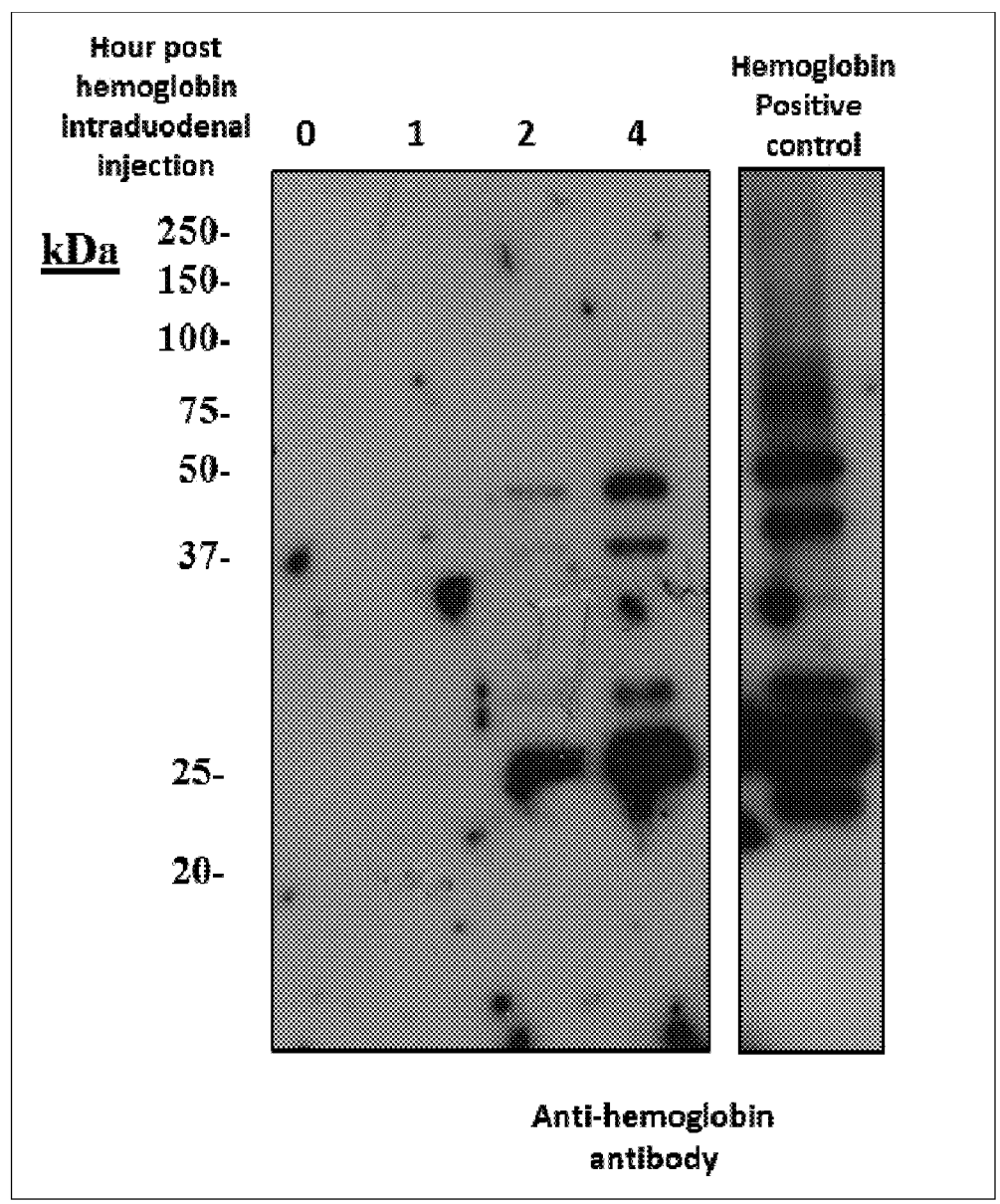
FIG. 11 Western blot images of hemoglobin detection from plasma samples after intraduodenal administration of the lyophilized hemoglobin formulation F7 in rats.

In one embodiment, intraduodenal administration of the lyophilized hemoglobin formulation F7 (70 mg/mL EGTA, 4.5 mg/mL PPS, 25 mg/mL SBTI, 4% w/v HPβCD, 6% w/v sucrose) is performed. Rats are anesthetized and jugular vein cannulation is performed for blood sampling. A midline incision is made in the abdomen and the duodenum is located. Approximately 15 cm of the duodenum is tied with sutures and the saline-dissolved of the lyophilized hemoglobin formulation F7 is injected into the duodenum lumen with a single dosage of 0.2 g/kg. The intestine is returned to its normal position and abdomen is suture closed. Blood samples are taken at different time points (0, 1, 2, 3, and 4 hours post intraduodenal administration). Hemoglobin is detected from the plasma samples by Western Blot protein analysis method and the images are shown in FIG. 11. Hemoglobin protein is detected in plasma samples of 2 hours and 4 hours post intradoudenal administration of saline-dissolved of the lyophilized hemoglobin formulation F7.

Figure 12:
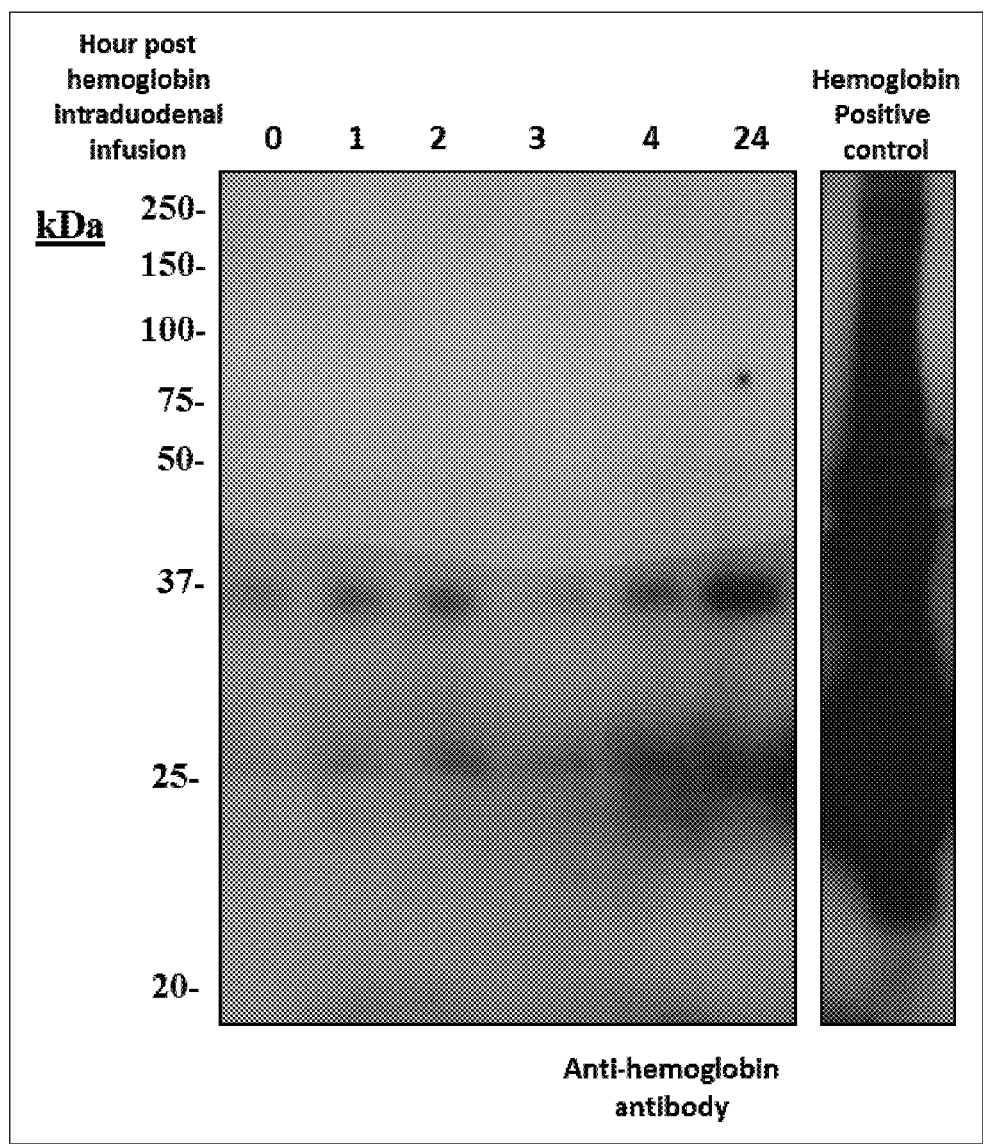
FIG. 12 Western blot images of hemoglobin detection from plasma samples after intraduodenal infusion of the lyophilized hemoglobin formulation F7 in rats.

In another embodiment, intraduodenal absorption of the lyophilized hemoglobin formulation F7 (70 mg/mL EGTA, 4.5 mg/mL PPS, 25 mg/mL SBTI, 4% HPβCD, 6% sucrose) is studied. Rats are anesthetized and jugular vein cannulation for blood sampling is performed. Meanwhile, a catheter is inserted into the rat duodenum lumen for transferring the lyophilized hemoglobin formulation F7 (saline-dissolved) via infusion at a single dosage of 0.2 g/kg. Rat duodenum is not died with sutures and the lyophilized formulation F7 hemoglobin solution is infused at a rate of 0.8 ml/hr. This catheterization facilitates dosing (single and multiple) in conscious freely moving rats after anesthetization. Blood samples are taken at different time points (0, 1, 2, 3, 4 and 24 hours post hemoglobin administration). Hemoglobin is detected from the plasma samples by Western Blot protein analysis method and the images are shown in FIG. 12. Hemoglobin protein is not detected in plasma samples at different time points post hemoglobin infusion of saline-dissolved of the lyophilized formulation F7 via catheter. In conclusion, the lyophilized formulation F7 enables delivery of hemoglobin from intestine into blood in this animal model, while mucosal adhesion is critical for its absorption.

Figure 13:
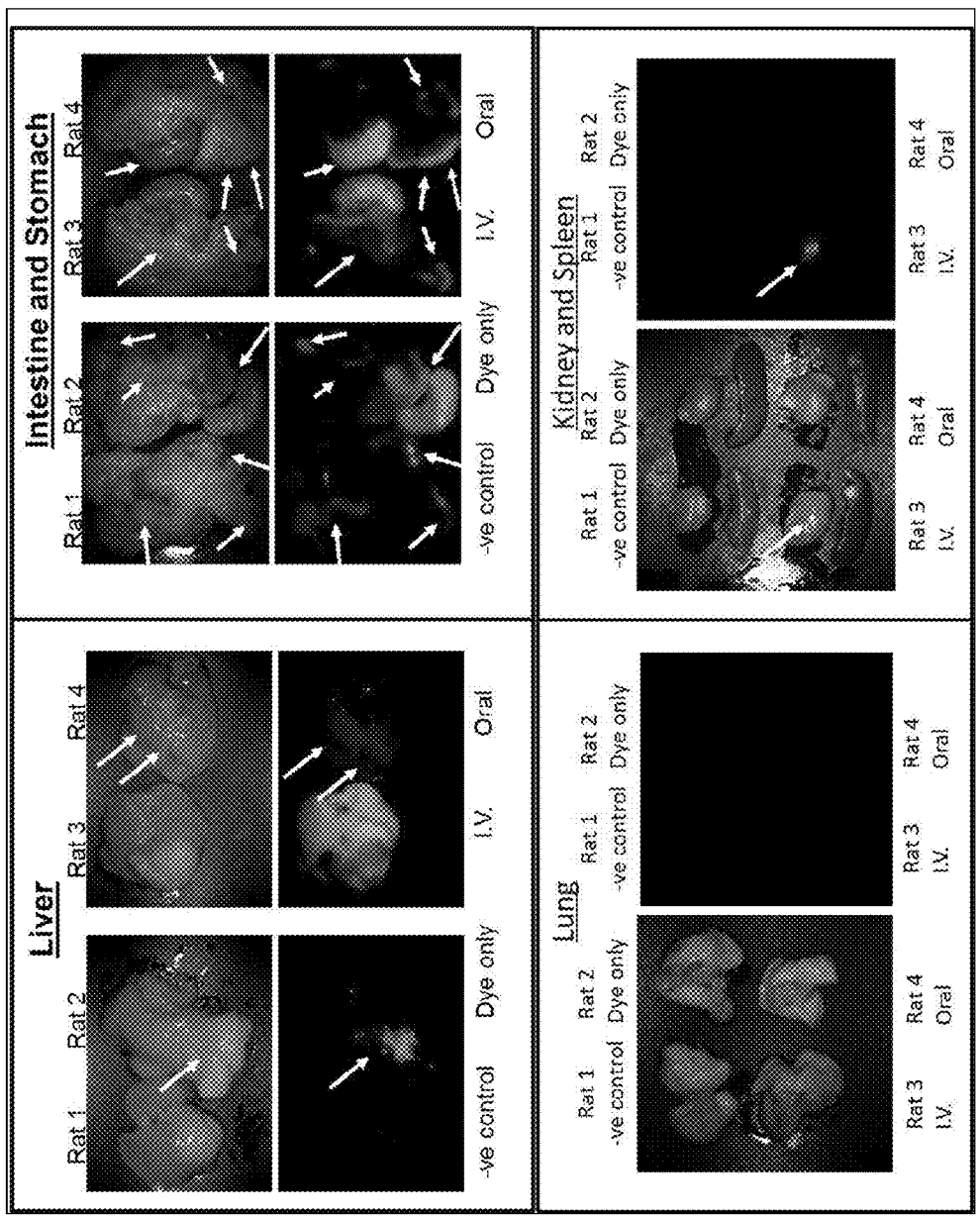
FIG. 13 Localization of fluorescence-labeled hemoglobin in different organs by different administrative routes. Arrows indicate the fluorescent signal.

Two hypothesized potential reasons of low hemoglobin absorbed into blood stream are: (1) accumulation of hemoglobin in the liver; (2) digestion and elimination in other excretory routes. In one embodiment, in vivo fluorescence imaging is performed to study the biodistribution of hemoglobin by intravenous injection or oral administration of the lyophilized formulation F7 to SD rats. One rat is a negative control without any administration (Rat 1), while other three rats are administered with inactivated dye intravenously (Rat 2), with fluorescent-labeled hemoglobin intravenously (Rat 3; 0.2 g/kg), and with fluorescent-labeled hemoglobin encapsulated into an enteric coated capsule orally (Rat 4; 0.2 g/kg), respectively. Ex vivo fluorescent images of different organs (liver, intestine, stomach, lung, spleen and kidney) are presented in FIG. 13. Fluorescent labeled hemoglobin is found to be localized at the intestine and stomach by intravenous and oral administrative routes. Meanwhile, only intravenous injection can deliver hemoglobin to the liver in this animal model. Inconclusive result observed in stomach is probably due to the background signal from the fluorescence dye. It shows that mucosal adhesion and absorption of hemoglobin is critical for its delivery into blood stream.

Figure 14:
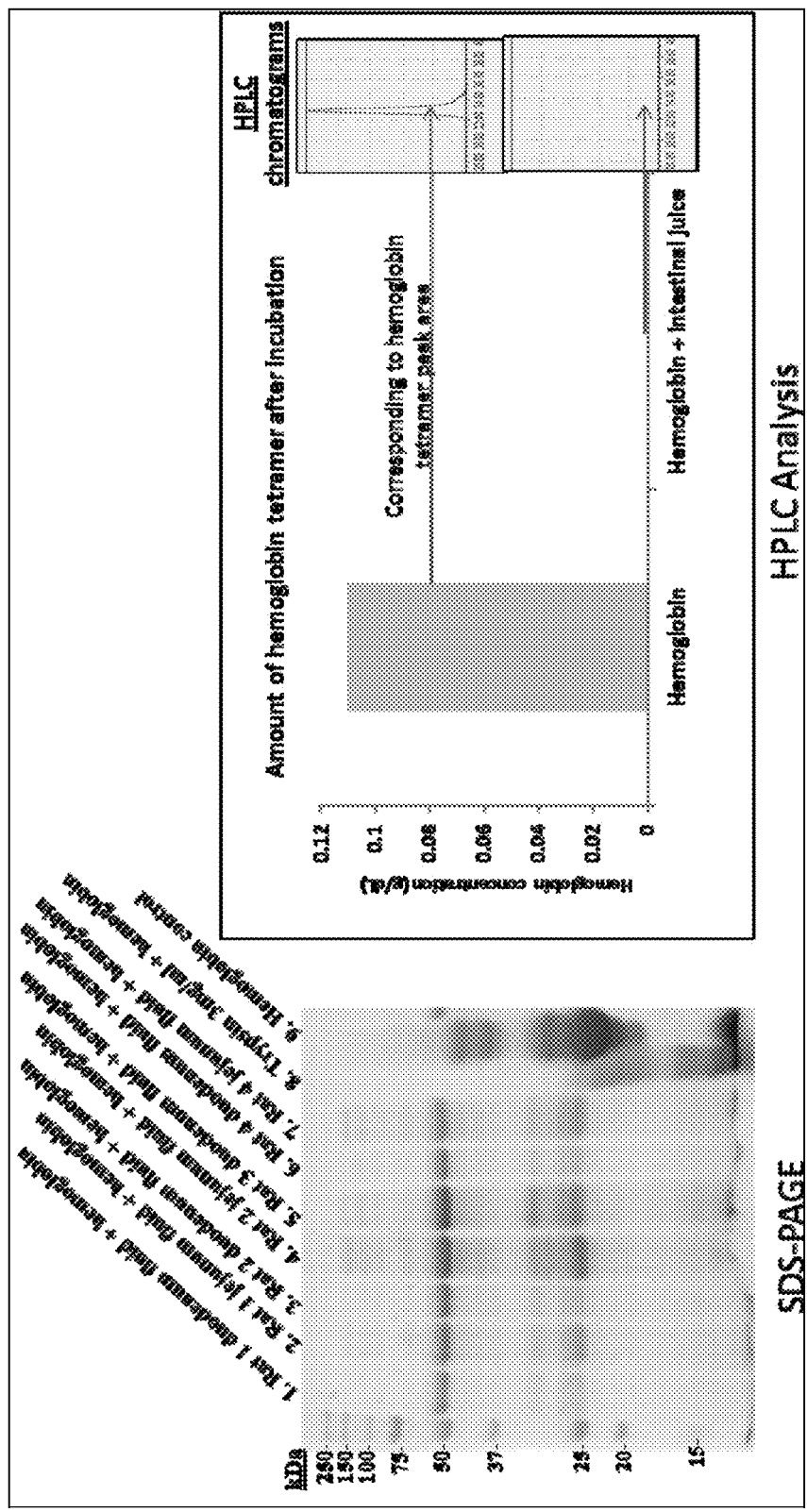
FIG. 14 SDS-PAGE images and HPLC analysis of hemoglobin tetramer of the lyophilized formulation F7 after proteolytic digestion with intestinal juices.

In one embodiment, the enzymatic activity of proteases in duodenum (pH 5-6) and jejunum (pH 6-7) on the lyophilized hemoglobin formulation is investigated. Duodenum fluid and jejunum fluid is collected from rats and incubated with the lyophilized hemoglobin formulation at 37° C. for 1 hour. Integrity and amount of hemoglobin tetramer is detected by SDS-PAGE and HPLC analysis (FIG. 14). No hemoglobin tetramer band is detected in the collected duodenum juice and jejunum juice (lanes 1-7) on the SDS-PAGE image. In HPLC analysis, hemoglobin tetramer is not detected in the intestinal juice. These results show that the lyophilized hemoglobin formulation is susceptible to enzymatic activity of proteases of small intestinal juice in the present animal model.

Figure 15:
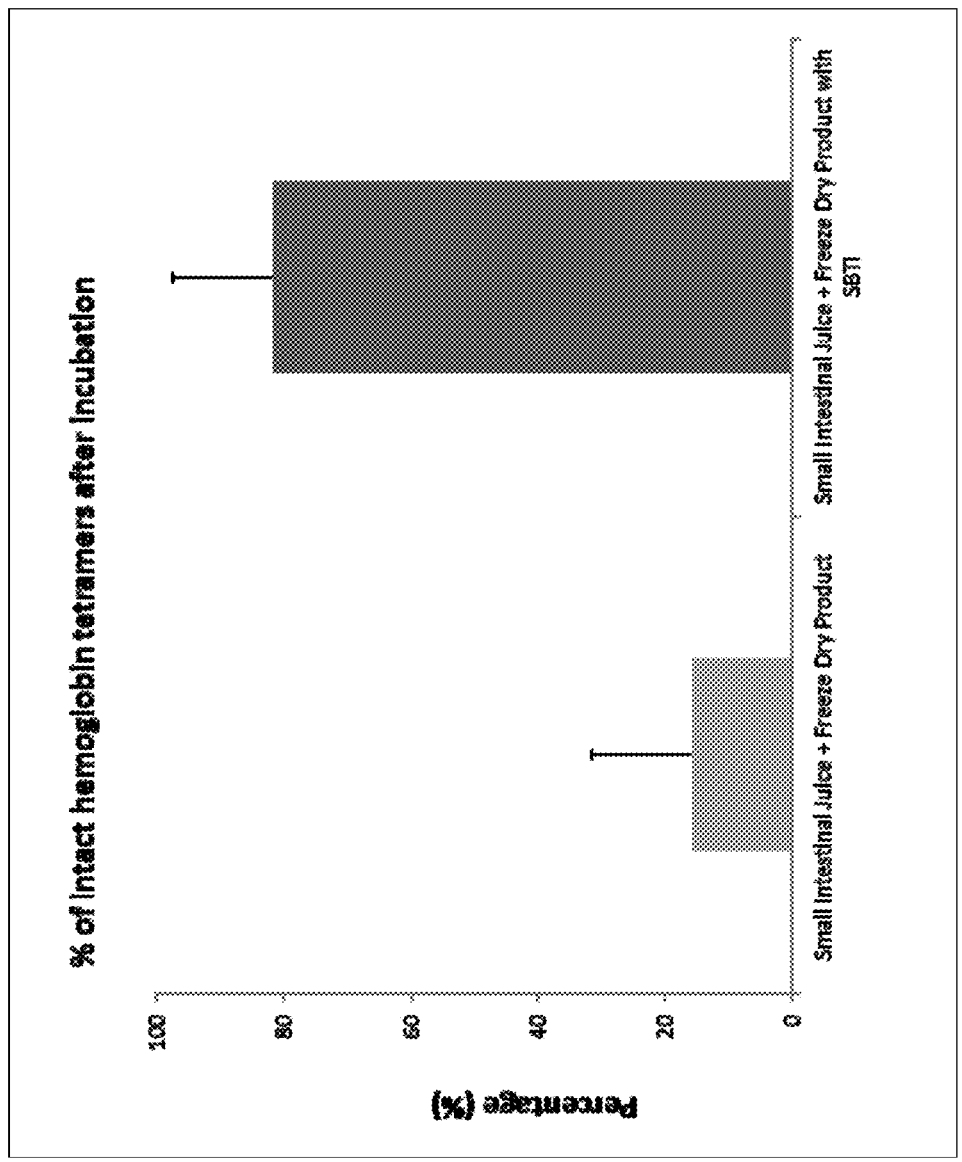
FIG. 15 HPLC analysis of hemoglobin tetramer of the lyophilized formulation F7 (with and without SBTI supplementation) after proteolytic digestion with intestinal juices.

In another embodiment, the efficacy of soybean trypsin inhibitor (SBTI) in protecting the lyophilized hemoglobin formulation against enzymatic digestion by small intestinal juice is investigated. Small intestinal juice is incubated with the lyophilized hemoglobin formulation F7, and with or without SBTI supplementation, at 37° C. for 1 hour. The amount of hemoglobin tetramer is detected by HPLC analysis after incubation (FIG. 15). Only 16% of the hemoglobin tetramer remains intact for its the lyophilized formulation without SBTI after incubating with intestinal juice. However, the lyophilized hemoglobin formulation supplemented with SBTI shows 82% of intact hemoglobin tetramers remaining after incubating with intestinal juice. These results show that the supplementation of soybean trypsin inhibitor (SBTI) in the lyophilized formulation F7 is effective in protecting hemoglobin against enzymatic digestion of intestinal juice.

Figure 3:
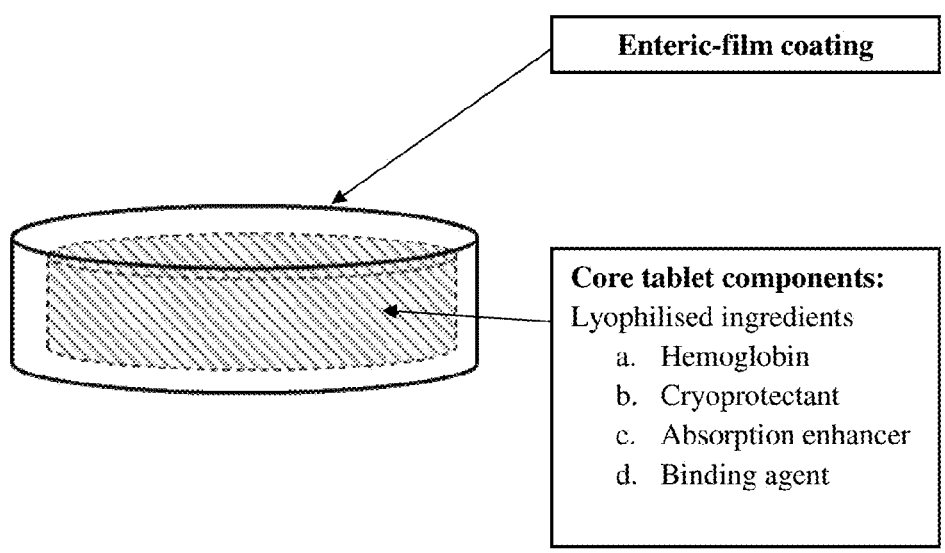
FIG. 3 shows the structure of enteric-coated hemoglobin tablet.

In another embodiment, lyophilized hemoglobin solid mixture is pressed into a core tablet, followed by an enteric film coating. The core tablet described herein uses lyophilized hemoglobin mixture as the active ingredient and other tablet forming excipients such as lactose monohydrate, polyvinylpyrrolidone, magnesium stearate, microcrystalline cellulose, anhydrous dibasic calcium phosphate. Optional excipients such as ethylcellulose, cellulose esters, poly(methacrylates) can be added to the lyophilized hemoglobin solid mixture to achieve a sustained release of hemoglobin and hence sustained delivery of oxygen to tissues. The thoroughly mixed powders are loaded to a tablet press machine, single-punch tablet press, or rotary tablet press to form the core tablet, which is then film coated by an enteric coating material, including poly(methacrylic acid)-poly(methyl methacrylate) copolymer, hydroxypropyl methylcellulose phthalate and cellulose acetate phthalate. FIG. 3 is a schematic diagram showing the basic structure of the enteric-coated tablet of the present invention. Compared to intravenous delivery of peptides or proteins, oral delivery has an advantage in pharmacokinetics because an oral delivery system enables controlled release of peptide or protein from the carriers. Such a controlled release mode of delivery of peptide or protein drug is unavailable in direct intravenous delivery. For hemoglobin being introduced into the vascular system, a controlled release and sustained elevation of the hemoglobin concentration in the blood has a greater physiological benefit than that from a sudden substantial increase of free hemoglobin in the injection site from direct injection. A rapid increase in the hemoglobin level increases the chance of developing side effects such as extravasation, myocardial infarction and renal toxicity.

The heme group of hemoglobin in HBOC consists of an iron (Fe) ion (charged atom) held in a heterocyclic ring. In addition to delivering oxygen to the human body by HBOC, the heme group can provide heme iron to the body to aid in the production of more red blood cells. Acetazolamide, steroids and *Rhodiola* cannot provide heme iron to the body.

Oral delivery of HBOCs is a non-invasive, convenient and efficient way to prevent or treat HAS, and therefore, it is favorable for people to take before or during travel from a sea level region to a high altitude region. Absorption of undegraded hemoglobin in intestinal tract, skipping de novo synthesis of hemoglobin, increases the oxygen-carrying capacity of blood thus increasing the rate of acclimatization. The orally-deliverable HBOCs can also be used to treat acute anemia due to blood loss or to prepare individuals for physically-demanding activities in normal or low oxygen supply atmosphere, e.g. for athletes, astronauts, divers, or navy personnel stationed in submarines. Improving tissue oxygenation by HBOCs is further useful for preventing/treating tissue ischemia, and promotes wound healing, such as diabetic foot ulcers. While the foregoing invention has been described with respect to various embodiments, such embodiments are not limiting. Numerous variations and modifications would be understood by those of ordinary skill in the art. Such variations and modifications are considered to be included within the scope of the following claims.

The following references relate to various aspects of the present invention and are incorporated by reference herein:

Artursson, P., et al. "Effect of chitosan on the permeability of monolayers of intestinal epithelial cells (Caco-2)." *Pharm Res.*, 1994, 11: 1358-1361.

Baek et al. "Hemoglobin-driven pathophysiology is an in vivo consequence of the red blood cell storage lesion that can be attenuated in guinea pigs by haptoglobin therapy." *The Journal of Clinical Investigation*, 2012, 122(4): 1444-1458.

Ballard, T. S., et al. "Regulation of tight-junction permeability during nutrient absorption across the intestinal epithelium." *Annu. Rev. Nutr*, 1995, 15: 35-55.

Barnikol, W. K., et al. "Complete healing of chronic wounds of a lower leg with haemoglobin spray and regeneration of an accompanying severe dermatoliposclerosis with intermittent normobaric oxygen inhalation (INBOI): a case report." *Ger Med Sci.*, 2011, 9 (DOI: 10.3205/000131).

Barrett, K. E., et al. "New Delhi: Tata-McGraw-Hill." *Ganong's Review of Medical Physiology*, 2009, $23^{rd}$ edition, pp. 619-20.

Becket, G., et al. "Improvement of the in vitro dissolution of praziquantel by complexation with $\alpha$-, $\beta$-, $\gamma$-cyclodextrins." *International Journal of Pharmaceutics*, 1999, 179(1): 65-71.

Blancher, C., et al. "Relationship of Hypoxia-inducible Factor (HIF)-1$\alpha$ and HIF-2$\alpha$ Expression to Vascular Endothelial Growth Factor Induction and Hypoxia Survival in Human Breast Cancer Cell Lines." *Cancer Res.*, 2000, 60: 7106-113.

Bonaventura, C., et al. "Allosteric effects on oxidative and nitrosative reactions of cell-free hemoglobin." *IUBMB Life*, 2007, 59(8-9): 498-505.

Brunel, F., et al. "Self-assemblies on chitosan nanohydrogels." *Macromol Biosci.*, 2010, 10(4): 424-432.

Cicco, G., et al. "Wound healing in diabetes: hemorheological and microcirculatory aspects." *Adv Exp Med Biol.* 2011, 701: 263-269.

Dünnhaupt, et al. "Distribution of thiolated mucoadhesive nanoparticles on intestinal mucosa." *International Journal of Pharmaceutics*, 2011, 408 (1-2): 191-199

Gupta, V., et al. "A permeation enhancer for increasing transport of therapeutic macromolecules across the intestine." *Journal of Controlled Release,* 2013, 172(2): 541-549.

Hackett, P. H., et al. "Dexamethasone for prevention and treatment of acute mountain sickness." *Aviat space Environ Med.,* 1988, 59: 950-954.

Hiromi, Sakai, et al. "Review of Hemoglobin-Vesicles as Artificial Oxygen Carriers." *Artificial organs,* 2009, 33(2): 139-145.

Honary, S., et al. "Effect of zeta potential on the properties of nano-drug delivery systems—a review (part 2)". *Tropical Journal of Pharmaceutical Research,* 2013, 12 (2): 263-273

Iwasaki, N, et al. "Feasibility of polysaccharide hybrid materials for scaffolds in cartilage tissue engineering: evaluation of chondrocyte adhesion to polyion complex fibers prepared from alginate and chitosan." *Biomacromolecules,* 2004, 5(3): 828-833.

Levien, L. J. "South Africa: clinical experience with Hemopure." *ISBT Science Series,* 2006, 1(1): 167-173.

Lin, Y. H., et al. "Multi-ion-crosslinked nanoparticles with pH-responsive characteristics for oral delivery of protein drugs." *J Control Release.,* 2008: 132(2), 141-149.

Makhlof, A., et al. "Design and evaluation of novel pH-sensitive chitosan nanoparticles for oral insulin delivery." *Eur J Pharm Sci.,* 2011, 42(5): 445-451.

Natanson, C., et al. "Cell-free hemoglobin-based blood substitutes and risk of myocardial infarction and death—A meta-analysis." *J Amer. Med. Assoc.,* 2008, 299(19): 2304-2312.

Niederhofer, A., et al. "A method for direct preparation of chitosan with low molecular weight from fungi." *Eur J Pharm Biopharm,* 2004, 57: 101-105.

Paralikar, Swapnil J., et al. "High-altitude medicine." *Indian J Occup Environ Med.,* 2010, 14(1): 6-12.

Remy, B., et al., "Red blood cell substitutes: fluorocarbon emulsions and hemoglobin emulsions." *British Medical Bulletin,* 1999, 55: 277-298.

Richard, A., et al. "Poly(glutamic acid) for biomedical applications." *Crit Rev Biotechnol,* 2001, 21: 219-232.

Sonaje, K., et al. 'Enteric-coated capsules filled with freeze-dried chitosan/poly(gamma-glutamic acid) nanoparticles for oral insulin delivery." *Biomaterials,* 2010, 31(12): 3384-3394.

Sudarshan, N., et al. "Antibacteri action of chitosn." *Food Biotechnology,* 1992, 6(3): 257-272.

Wong, B. L., et al. (2011), U.S. Pat. Nos. 7,932,356, 7,989,593, 8,048,856 & 8,084,581

Wong, B. L., et al. (2012), U.S. Pat. No. 8,106,011

Xiu, R. (2002), U.S. Pat. No. 6,399,116

Yamamoto, A., et al. "Effects of various protease inhibitors on the intestinal absorption and degradation of insulin in rats." *Pharmaceutical Research,* 1994, 11(10): 1496-1500.

What is claimed is:

1. A hemoglobin formulation for lyophilization to form lyophilized hemoglobin particles or powders comprising a hemoglobin-based oxygen carrier, at least one of stabilizers or cryoprotectants, at least two absorption enhancers, and a protease inhibitor, wherein said at least two absorption enhancers are ethylene glycol tetraacetic acid and palmitoyl dimethyl ammonio propane sulfonate.

2. The hemoglobin formulation of claim 1, wherein said at least one of stabilizers or cryoprotectants consist essentially of sucrose and hydroxypropyl-β-cyclodextrin.

3. The hemoglobin formulation of claim 1, wherein said protease inhibitor is soybean trypsin inhibitor.

4. The hemoglobin formulation of claim 1, wherein said hemoglobin-based oxygen carrier comprises non-polymeric tetrameric hemoglobin molecules.

5. The hemoglobin formulation of claim 2, wherein said sucrose is in a concentration of 6% w/v and said hydroxypropyl-β-cyclodextrin is in a concentration of 4% w/v.

6. The hemoglobin formulation of claim 1, wherein said ethylene glycol tetraacetic acid is in a concentration of 70 mg/mL and said palmitoyl dimethyl ammonio propane sulfonate is in a concentration of 4.5 mg/mL.

7. The hemoglobin formulation of claim 3, wherein said soybean trypsin inhibitor is in a concentration of 25 mg/mL.

8. The hemoglobin formulation of claim 1, wherein said hemoglobin-based oxygen carrier is in a concentration of 300 mg/mL.

9. The hemoglobin formulation of claim 1, further comprising N-acetyl cysteine as an antioxidant.

10. The hemoglobin formulation of claim 1, wherein said lyophilization comprises the following steps to form said lyophilized hemoglobin particles or powders are formed:

b1) freezing said hemoglobin formulation at −60° C. for 2 hours;

b2) subsequent freezing at −60° C. for 6 hours;

b3) subjecting to chamber vacuum under a pressure of 0.5 mbar at −60° C. for 2 hours;

b4) primary drying under a pressure of 0.5 mbar at −10° C. for 2 hours;

b5) subsequent primary drying under a pressure of 0.5 mbar at −10° C. for 10 hours;

b6) additional primary drying under a pressure of 0.5 mbar at 0° C. for 1 hour;

b7) further primary drying under a pressure of 0.5 mbar at 0° C. for 8 hours;

b8) secondary drying under a pressure of 0.2 mbar at 15° C. for 1.5 hours;

b9) subsequent secondary drying under a pressure of 0.08 mbar at 15° C. for 8 hours;

b10) additional secondary drying under a pressure of 0.08 mbar at 25° C. for 1 hour; and b11) further secondary drying under a pressure of 0.001 mbar at 25° C. for 6 hours.

11. An orally administrable capsule or tablet encapsulating lyophilized hemoglobin particles or powders formed by the hemoglobin formulation of claim 1.

12. A method for enhancing tissue oxygenation via increasing permeability of lyophilized hemoglobin particles or powders across epithelial cells along the intestinal tract comprising administering the orally administrable capsule or tablet encapsulating lyophilized hemoglobin particles or powders of claim 11 to a subject in need thereof.

13. The method of claim 12, wherein said orally administrable capsule encapsulating lyophilized hemoglobin particles or powders is in a concentration of 0.2 g/kg of body weight of said subject and said administering is via oral administration.

14. The orally administrable capsule or tablet of claim 11, wherein said orally administrable capsule is an enteric coated capsule containing 9 mg of said lyophilized hemoglobin particles or powders.

15. The method of claim 12, wherein said orally administrable capsule is orally administered at a dose of 0.9 g/kg to said subject.

* * * * *